(12) United States Patent
Coursey et al.

(10) Patent No.: US 10,590,495 B2
(45) Date of Patent: Mar. 17, 2020

(54) METHODS, DEVICES, AND SYSTEMS FOR PROCESSING MULTIPLE ASSAYS

(71) Applicant: Canon U.S.A., Inc., Melville, NY (US)

(72) Inventors: Johnathan S. Coursey, Rockville, MD (US); Kenton C. Hasson, Germantown, MD (US); Brian Bean, Baltimore, MD (US); Scott Corey, Hydes, MD (US)

(73) Assignee: Canon U.S.A., Inc., Melville, NY (US)

( * ) Notice: Subject to any disclaimer, the term of this patent is extended or adjusted under 35 U.S.C. 154(b) by 140 days.

(21) Appl. No.: 15/905,330

(22) Filed: Feb. 26, 2018

(65) Prior Publication Data

US 2018/0179602 A1 Jun. 28, 2018

Related U.S. Application Data

(62) Division of application No. 13/838,411, filed on Mar. 15, 2013, now Pat. No. 9,903,003.

(51) Int. Cl.
*B01L 7/00* (2006.01)
*C12Q 3/00* (2006.01)
*C12Q 1/686* (2018.01)
*B01L 3/00* (2006.01)

(52) U.S. Cl.
CPC .......... *C12Q 3/00* (2013.01); *B01L 3/502784* (2013.01); *B01L 7/525* (2013.01); *C12Q 1/686* (2013.01); *B01L 2200/148* (2013.01); *B01L 2300/0816* (2013.01); *B01L 2300/0867* (2013.01); *B01L 2300/1827* (2013.01); *B01L 2400/0487* (2013.01)

(58) Field of Classification Search
None
See application file for complete search history.

(56) References Cited

U.S. PATENT DOCUMENTS

| | | |
|---|---|---|
| 2007/0062583 A1 | 3/2007 | Cox et al. |
| 2007/0231799 A1* | 10/2007 | Knight .............. B01L 3/502715 435/6.11 |
| 2008/0003588 A1 | 1/2008 | Hasson et al. |
| 2009/0227007 A1* | 9/2009 | Takahashi ......... B01L 3/502715 435/287.2 |
| 2009/0318306 A1* | 12/2009 | Hasson ............. B01L 3/502784 506/12 |
| 2010/0028980 A1 | 2/2010 | Hasson et al. |
| 2011/0124114 A1 | 5/2011 | Ermantraut et al. |
| 2012/0052560 A1* | 3/2012 | Knight .............. B01L 3/502784 435/286.1 |
| 2012/0058460 A1 | 3/2012 | Coursey et al. |
| 2012/0058519 A1 | 3/2012 | Knight et al. |
| 2013/0017544 A1 | 1/2013 | Eckhardt et al. |

FOREIGN PATENT DOCUMENTS

| | | |
|---|---|---|
| JP | 2010-524430 A | 7/2010 |
| WO | 2008/143646 A2 | 11/2008 |
| WO | 2012/030995 A2 | 3/2012 |
| WO | 2012/031050 A1 | 3/2012 |

* cited by examiner

*Primary Examiner* — Aaron A Priest
(74) *Attorney, Agent, or Firm* — Rothwell, Figg, Ernst & Manbeck, P.C.

(57) ABSTRACT

Methods, devices, and systems for performing polymerase chain reaction (PCR) amplification and melt data acquisition according to a single slug approach in which a single slug in a microfluidic channel fills an entire thermal zone of the microfluidic channel, and the thermal zone used for both PCR temperature cycling and melt data acquisition. A detector may be configured to detect fluorescence from the thermal zone during the PCR temperature cycling for real-time PCR and/or during temperature ramping in the melt data acquisition. Slug position control may be achieved by detecting leading or trailing edges in a slug build target zone into which a slug passes after passing through the thermal zone. The single slug approach may break coupling between one or more events of the PCR amplification and melt data acquisition and enable events to be independently optimized.

64 Claims, 23 Drawing Sheets

METHODS, DEVICES, AND SYSTEMS FOR PROCESSING MULTIPLE ASSAYS

CROSS-REFERENCE TO RELATED APPLICATION

The present application is a divisional of U.S. patent application Ser. No. 13/838,411, filed on Mar. 15, 2013, which is incorporated by reference in its entirety.

BACKGROUND

Field of the Invention

The present invention relates to methods, devices, and systems for fluid processing in a microfluidic device. More particularly, aspects of the present invention relate to methods, devices, and systems utilizing a single slug approach in which a single slug fills a thermal zone of a microfluidic channel, and the thermal zone is used for both PCR amplification melt data acquisition.

Description of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, identification of crime scene features, the ability to propagate industrial organisms, and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. Polymerase chain reaction (PCR) is a well-known technique for amplifying deoxyribonucleic acid (DNA). With PCR, one can produce millions of copies of DNA starting from a single template DNA molecule. The PCR process includes phases of "denaturation," "annealing," and "extension." These phases are part of a cycle which is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

The PCR process phases of denaturing, annealing, and extension occur at different temperatures and cause target DNA molecule samples to replicate themselves. Temperature cycling (thermocyling) requirements vary with particular nucleic acid samples and assays. In the denaturing phase, a double stranded DNA (dsDNA) is thermally separated into single stranded DNA (ssDNA). During the annealing phase, primers are attached to the single stranded DNA molecules. Single stranded DNA molecules grow to double stranded DNA again in the extension phase through specific bindings between nucleotides in the PCR solution and the single stranded DNA. Typical temperatures are 95° C. for denaturing, 55° C. for annealing, and 72° C. for extension. The temperature is held at each phase for a certain amount of time, which may be a fraction of a second up to a few tens of seconds. The DNA is doubled at each cycle, and certain applications may require numerous (e.g., 20 to 40 or more) cycles to produce enough DNA. To have good yield of target product, one has to accurately control the sample temperatures at the different phases to a specified degree.

The multi-slug approach is a high throughput approach to performing PCR and other amplification reactions in microfluidic devices, as well detecting and analyzing amplified nucleic acids in or on the devices. The multi-slug approach creates a sequence of short slugs (i.e., a slug train) in a microfluidic channel of a microfluidic device. Several slugs share a PCR thermal zone ("Zone 1") in which the temperature of the slugs is cycled to perform a PCR amplification before passing into a melt thermal zone ("Zone 2") in which the temperature of the slugs is ramped to melt any DNA in the slugs (i.e., dissociate the strands of any DNA in the slugs).

A multi-slug system may have a cartridge with one or more microfluidic channels. Each of these channels may have a three branched (i.e., Y-shaped or T-shaped) topology that is used to created short slugs inside the PCR chip. The slugs alternate between a test/sample slug and a flow marker or "blanking" slug. Fluorescence emitted from the blanking slugs may have a different color than fluorescence emitted by the sample slugs. The color difference enables the blanking slugs to be spatially imaged and used for slug position sensing. Information about the slug position may be fed back to adjust the pressure applied to the downstream end of the channel and, thereby, control the positions of the slugs.

FIG. 11 illustrates an exemplary timing sequence of slugs progressing through a channel of a reaction chip ("Uchip") of a system implementing a simplified multi-slug approach in which no more than two sample slugs are in the PCR thermal zone (Zone 1) at a given time. TABLE 1 (below) shows the events occurring during steps of a simplified multi-slug processing in a multi-slug system having a microfluidic device with an interface chip and a reaction chip. In Table 1 below, important events are shown in bold.

TABLE 1

| Step # | Interface Chip Flow Events | Reaction Chip Flow Events | Zone 1 Events | Zone 2 Events | Exemplary Time (s) |
| --- | --- | --- | --- | --- | --- |
| 1 | — | Pull In Sample Slug | PCR | — | 100 |
| 2 | Load Blanking Solution | Hold Sample Slug | PCR | — | 100 |
| 3 | — | Pull In Blanking Slug | PCR | — | 100 |
| 4 | Load Sample Solution | Hold Blanking Slug | PCR | Melt | 100 |

As illustrated in FIG. 11 and in TABLE 1, the multi-slug system is highly coupled, with multiple important events occurring at the same time. As multiple important events occur at the same time, there is a need to balance flow, PCR, and melt requirements, and no single event is truly optimized.

The design concept of the multi-slug approach was based on having multiple slugs in the PCR thermal zone (Zone 1) to increase throughput. However, in practice the multi-slug approach may have some drawbacks. The multi-slug timing may be problematic because of the need to always compromise and balance the conflicting requirements of two or three concurrent events. The multi-slug approach also uses at least two sets of slugs (i.e., two samples and two blanks) on the reaction chip at the same time. Furthermore, the small slugs may be difficult to align, which may lead to the need for a time consuming slug training step (e.g., using start-up slugs).

The following describes some shortcomings that may be present in the multi-slug design:

1. Several slugs in a channel share the PCR thermal zone (Zone 1) at the same time, which means the same thermocycling conditions must be used for all of the slugs in the PCR thermal zone. This may be limiting to assay optimization.

2. As the PCR thermal zone (Zone 1) is cycling the temperatures to perform PCR amplification as the slugs pass through the entirety of the PCR zone thermal, the temperature in the PCR thermal zone must be uniform across the entirety of PCR thermal zone, which may be, for instance, 14.75 mm in length. However, obtaining a uniform temperature across the entirety of PCR thermal zone may be difficult due to thermal gradients, variations in heat sink attachment, etc.

3. Slugs spend a portion of the thermal cycling time straddling the leading and trailing edges of PCR thermal zone (Zone 1). See, e.g., FIG. 11. This results in a varying number of cycles for different portions of the slug. Moreover, temperature may be less uniform at the edges of the PCR thermal zone, and portions of the slug are subjected to thermal cycling at non-optimal temperatures which may result in non-specific amplification and/or overall low efficiency.

4. The design is not compatible with hot starting the polymerase enzyme or providing a longer initial denaturation step because several slugs share the heater of the PCR thermal zone (Zone 1) at the same time.

5. Simultaneously running PCR thermal heaters in the PCR thermal zone (Zone 1) and melt thermal heaters in the melt thermal zone (Zone 2) presents certain challenges. For example, a pumping effect is caused by the expansion of an aqueous solution in a channel when heated. Rapid cycling of the PCR thermal zone (Zone 1) temperature produces an oscillatory pumping effect on the fluid in the channel that, in some circumstances, can adversely affect the quality of melt data obtained from the melt thermal zone (Zone 2).

6. Slug length varies as slugs cross the chip due to variations in the depth of the microfluidic channels. In other words, slugs lengthen or shorten if the microchannels become more or less shallow. The variation in slug length makes accurate positioning of the slugs in the melt thermal zone (Zone 2) problematic, and a complex and time consuming position calibration approach may be required to mitigate the variation in slug length.

7. The short slugs used in the multi-slug approach may have a greater propensity for unwanted diffusion effects (e.g., amplicon carryover).

8. PCR product that is created in the PCR thermal zone (Zone 1) may not make it to the melt thermal zone (Zone 2) for analysis because of dispersion that occurs as the fluid is moved.

9. The multi-slug system requires continuous active feedback control of the pressure applied to the downstream end of the reaction chip. If for any reason control of the pressure fails, the slug train in a channel can undergo a loss of positioning control. Generally speaking, there may be no way to recover use of the particular channel for the slug train for which pressure control was lost.

10. Any motion that may exist due to active continuous flow control may result in significant artifacts in melt curves as the short slug length means the product and fluorescence change rapidly.

11. In certain color imaging systems, there may be cross-talk between the color planes. Having short slugs of different color may increase the cross-talk and bleed over between colors.

12. Changing the flow rates requires a corresponding change in PCR and melt timing. This may result in un-wanted delays where the fluid sits before the melt (perhaps in a region of the chip which is not rigorously controlled in terms of temperature).

13. Changing the PCR timing requires a corresponding change in the flow rates. This is undesirable because the microfluidics may not function as reliable at the flow rates necessitated by the PCR timing.

14. There may be no time for a long melt or repeating a melt because the slug train must keep advancing.

15. The multi-slug system may be slow to start up because of the difficulty in creating the first short slugs and the need for slug position calibration.

16. The multi-slug system may be slow to reflex to a melt result because slugs are already in the queue.

17. Two thermal zones (i.e., a PCR thermal zone and a different melt thermal zone) may require twice as much hardware: data acquisition, signal conditioning, heat sink, cabling, etc.

18. The small size of the slugs, dispersion, and motion across PCR thermal zone (Zone 1) may make real time PCR highly problematic.

Accordingly, there is a need for improved methods, devices, and systems for processing slugs in microfluidic devices.

SUMMARY

In one aspect, the present invention provides methods, devices, and systems that implement a single slug approach to performing PCR amplification and melt data acquisition. In some embodiments utilizing the single slug approach, no more than one slug per microfluidic channel is present in a thermal zone of a microfluidic device, and the thermal zone may be used for both PCR amplification and melt data acquisition. That is, in some embodiments utilizing the single slug approach, a slug need not be moved from one thermal zone in which temperature cycling was performed to a different thermal zone for a temperature ramp. The single slug approach may break the coupling between events present in the multi-slug approach and enable processing events to be controlled independently, which may allow independent optimization of each event.

In one aspect, the present invention provides a method for performing polymerase chain reaction (PCR) amplification and melt data acquisition in a single slug reaction system. The method includes building a blanking slug by drawing a blanking solution into a microfluidic channel of a reaction chip of a microfluidic device until the leading edge of the blanking slug reaches a blanking slug building target region; building a sample slug by drawing a sample solution into the microfluidic channel of the reaction chip of the microfluidic device until the trailing edge of the blanking slug reaches a sample slug building target region; heating a portion of the sample slug in a thermal zone of the reaction chip to cycle the temperature of the portion of the sample slug in the thermal zone according to a PCR amplification profile; heating the portion of the sample slug in the thermal zone of the reaction chip according to a temperature ramp profile; and, during heating of the portion of the sample slug in the thermal zone according to the temperature ramp profile, measuring fluorescence from the portion of the sample slug in the thermal zone.

In some embodiments, the method may include performing a melt analysis to identify the melting temperature of a nucleic acid in the sample slug based on the fluorescence from the portion of the sample slug in the thermal zone measured during heating of the portion of the sample slug in the thermal zone according to the temperature ramp profile.

In some embodiments, the blanking slug may be a first blanking slug, the sample slug may be a first sample slug, the sample solution may be a first sample solution, and the method may include building a second blanking slug by drawing the blanking solution into the microfluidic channel of the reaction chip of the microfluidic device until the leading edge of the second blanking slug reaches the blanking slug building target region; building a second sample slug by drawing a second sample solution into the microfluidic channel of the reaction chip of the microfluidic device until the trailing edge of the second blanking slug reaches the sample slug building target region; heating a portion of the second sample slug in the thermal zone of the reaction chip to cycle the temperature of the portion of the sample slug in the thermal zone according to the PCR amplification profile; heating the portion of the sample slug in the thermal zone of the reaction chip according to the temperature ramp profile; and, during heating of the portion of the second sample slug in the thermal zone according to the temperature ramp profile, measuring fluorescence from the portion of the second sample slug in the thermal zone. The method may include performing a first melt analysis to identify the melting temperature of a nucleic acid in the first sample slug based on the fluorescence from the portion of the first sample slug in the thermal zone measured during heating of the portion of the first sample slug in the thermal zone according to the temperature ramp profile; and performing a second melt analysis to identify the melting temperature of a nucleic acid in the second sample slug based on the fluorescence from the portion of the second sample slug in the thermal zone measured during heating of the portion of the second sample slug in the thermal zone according to the temperature ramp profile.

In some embodiments, the method may include calibrating the microfluidic device. Calibrating the microfluidic device may include building a calibration blanking slug by drawing a calibration blanking solution into the microfluidic channel of the reaction chip of the microfluidic device until the leading edge of the calibration blanking slug reaches the blanking slug building target region; building a calibration test slug by drawing a calibration solution including a known sample into the microfluidic channel of the reaction chip of the microfluidic device until the trailing edge of the calibration blanking slug reaches the sample slug building target region; heating the portion of the calibration test slug in the thermal zone of the reaction chip according to the temperature ramp profile; during heating of the portion of the calibration test slug in the thermal zone according to the temperature ramp profile, measuring fluorescence from the portion of the calibration test slug in the thermal zone; and performing a calibration melt analysis to determine calibration coefficients.

In some embodiments, the method may include heating, for a second time, the portion of the sample slug in the thermal zone of the reaction chip according to the temperature ramp profile; during the second heating of the portion of the sample slug in the thermal zone according to the temperature ramp profile, measuring fluorescence from the portion of the sample slug in the thermal zone; and performing a melt analysis to identify the melting temperature of the nucleic acid in the sample slug based on the fluorescence from the portion of the sample slug in the thermal zone measured during the first heating of the portion of the sample slug in the thermal zone and the fluorescence from the portion of the sample slug in the thermal zone measured during the second heating of the portion of the sample slug in the thermal zone.

In some embodiments, the reaction chip may comprise a second zone, and slugs in the microfluidic channel of the reaction chip may reach the second zone after passing through the thermal zone. One or both of the blanking slug building target region and the sample slug building target region may be within the second zone of the reaction chip. The second zone is a second thermal zone. The microfluidic chip may include a first heating element associated with the thermal zone and a second heating element associated with the second zone, the first heating element may be used to heat the portion of the sample slug in the thermal zone of the reaction chip according to the PCR amplification and temperature ramp profiles. The microfluidic chip may include a heating element associated with the thermal zone, the first heating element may be used to heat the portion of the sample slug in the thermal zone of the reaction chip according to the PCR amplification and temperature ramp profiles, and the microfluidic chip may not comprise a heating element associated with second zone.

In some embodiments, the method may include, after building the sample slug, holding the sample slug in position until after heating of the portion of the sample slug in the thermal zone according to the temperature ramp profile is completed. In some embodiments, the method may include, after building the sample slug and before completion of heating of the portion of the sample slug in the thermal zone according to the temperature ramp profile, drawing the sample slug across the thermal zone, wherein the sample slug is drawn across the thermal zone with a flow rate slow enough that the sample slug remains in the thermal zone for the entirety of the heating according to the PCR amplification and temperature ramp profiles. In some embodiments, the method may include, after building the sample slug and before completion of heating of the portion of the sample slug in the thermal zone according to the temperature ramp profile, intermittently moving the sample slug. In some embodiments, the method may include, after building the sample slug and before completion of heating of the portion of the sample slug in the thermal zone according to the temperature ramp profile, moving the sample slug back and forth in the microfluidic channel of the reaction chip of the microfluidic device.

In some embodiments, the measured fluorescence from the portion of the sample slug in the thermal zone may be measured only from a region of interest within the thermal zone. The region of interest may be small relative to the size of the thermal zone. The region of interest may be in the center of the thermal zone. The region of interest may be within the middle 50% of the thermal zone. The region of interest may be located at the portion of the thermal zone where PCR amplification is most efficiently carried out.

In some embodiments, the method may include, during heating of the portion of the sample slug in the thermal zone of the reaction chip according to the PCR amplification profile, measuring fluorescence from the thermal zone. The method may include, during heating of the portion of the sample slug in the thermal zone of the reaction chip according to the PCR amplification profile, adjusting the PCR amplification profile based on the measured fluorescence. Adjusting the PCR amplification profile may include adjusting the number of temperature cycles of the PCR amplification profile or adjusting denaturation, annealing, or extension temperatures of the PCR amplification profile.

In some embodiments, the PCR amplification profile may be a hot start PCR amplification profile. During heating according to the PCR amplification and temperature ramp profiles, the sample slug may completely fill the thermal zone of the reaction chip. The method may include, after building the blanking slug and before building the sample slug, holding the leading edge of the blanking slug in position at the blanking slug building target region. The leading edge of the blanking slug may be held in place using image based feedback control.

In some embodiments, the method may include, after building the sample slug and before completion of heating according to the temperature ramp profile, holding the trailing edge of the blanking slug in position at the sample slug building target region. The trailing edge of the blanking solution may be held in place using image based feedback control.

In some embodiments, the method may include drawing the blanking solution into a microfluidic channel of an interface chip of the microfluidic device via an inlet port of the interface chip, wherein the blanking solution drawn into the microfluidic channel of the reaction chip of the microfluidic device to build the blanking slug is drawn from the microfluidic channel of the interface chip; drawing the sample solution into the microfluidic channel of the interface chip of the microfluidic device via the inlet port of the interface chip, wherein the sample solution drawn into the microfluidic channel of the reaction chip of the microfluidic device to build the sample slug is drawn from the microfluidic channel of the interface chip. Drawing the blanking solution into the microfluidic channel of the reaction chip of the microfluidic device may include filling a T-junction with the blanking solution from the microfluidic channel of the interface chip and drawing the blanking solution into the microfluidic channel of the reaction chip from the T-junction, and drawing the sample solution into the microfluidic channel of the reaction chip of the microfluidic device may include filling the T-junction with the sample solution from the microfluidic channel of the interface chip and drawing the sample solution into the microfluidic channel of the reaction chip from the T-junction. The method may include determining whether the blanking solution has filled the T-junction by detecting whether a leading edge of the blanking solution has reached a region of interest in the interface chip of the microfluidic device. The method may include determining whether the sample solution has filled the T-junction by detecting whether a trailing edge of the blanking solution has reached the region of interest in the interface chip of the microfluidic device.

In some embodiments, the blanking slug building target region and sample slug building target region may be within a region of interest in the reaction chip of the microfluidic device. The method may include, after heating the portion of the sample slug in a thermal zone of the reaction chip to cycle the temperature of the portion of the sample slug in the thermal zone according to the PCR amplification profile and before heating the portion of the sample slug in the thermal zone of the reaction chip according to the temperature ramp profile, heating the portion of the sample slug in the thermal zone of the reaction chip according to a de-naturing and re-naturing profile.

In another aspect, the present invention provides a single slug microfluidic reaction system. The single slug microfluidic reaction system may include a microfluidic device, a flow controller, a heating system, and a detection system. The microfluidic device may include a reaction chip. The flow controller may be configured to: build a blanking slug by drawing a blanking solution into a microfluidic channel of the reaction chip until the leading edge of the blanking slug reaches a blanking slug building target region; and build a sample slug by drawing a sample solution into the microfluidic channel of the reaction chip until the trailing edge of the blanking slug reaches a sample slug building target region. The heating system may include a heating element associated with a thermal zone of the reaction chip, and a heating controller. The heating controller may be configured to control the heating element to: heat a portion of the sample slug in the thermal zone of the reaction chip to cycle the temperature of the portion of the sample slug in the thermal zone according to a polymerase chain reaction (PCR) amplification profile; and heat the portion of the sample slug in the thermal zone of the reaction chip according to a temperature ramp profile. The detection system may be configured to, during heating of the portion of the sample slug in the thermal zone according to the temperature ramp profile, measure fluorescence from the portion of the sample slug in the thermal zone.

In some embodiments, the single slug microfluidic reaction system may include a melt analyzer configured to perform a melt analysis to identify the melting temperature of a nucleic acid in the sample slug based on the fluorescence from the portion of the sample slug in the thermal zone measured during heating of the portion of the sample slug in the thermal zone according to the temperature ramp profile.

In some embodiments, the reaction chip may include a second zone, and slugs in the microfluidic channel of the reaction chip may reach the second zone after passing through the thermal zone. One or both of the blanking slug building target region and the sample slug building target region may be within the second zone of the reaction chip. The second zone may be a second thermal zone. The heating element may be a first heating element, and the heating system may include a second heating element associated with the second thermal zone. However, in some embodiments, the microfluidic device may not comprise a heating element associated with the second thermal zone.

In some embodiments, the flow controller may configured to hold the sample slug in a fixed position during heating of the portion of the sample slug in the thermal zone according to the PCR amplification and temperature ramp profiles. The flow controller may be configured to, after building the sample slug, hold the sample slug in position until after heating of the portion of the sample slug in the thermal zone according to the temperature ramp profile is completed. However, in some embodiments, the flow controller may be configured to, after building the sample slug and before completion of heating of the portion of the sample slug in the thermal zone according to the temperature ramp profile, draw the sample slug across the thermal zone with a flow rate slow enough that the sample slug remains in the thermal zone for the entirety of the heating according to the PCR amplification and temperature ramp profiles or intermittently move the sample slug or move the sample slug back and forth in the microfluidic channel of the reaction chip of the microfluidic device.

In some embodiments, the detection system may be configured to, during heating of the portion of the sample slug in the thermal zone of the reaction chip according to the PCR amplification profile, measure fluorescence from the thermal zone. The heating controller may be configured to, during heating of the portion of the sample slug in the thermal zone of the reaction chip according to the PCR amplification profile, adjust the PCR amplification profile based on the measured fluorescence. Adjusting the PCR amplification profile may include adjusting the number of temperature cycles of the PCR amplification profile or adjusting denaturation, annealing, or extension temperatures of the PCR amplification profile.

In some embodiments, the PCR amplification profile may be a hot start PCR amplification profile. During heating according to the PCR amplification and temperature ramp profiles, the sample slug may completely fill the thermal zone of the microfluidic device.

The flow controller may be configured to, after building the blanking slug and before building the sample slug, hold the leading edge of the blanking slug in position at the blanking slug building target region. The leading edge of the blanking slug may be held in place using image based feedback control. The flow controller may be configured to, after building the sample slug and before completion of heating according to the temperature ramp profile, hold the trailing edge of the blanking slug in position at the sample slug building target region. The trailing edge of the blanking solution may be held in place using image based feedback control.

In some embodiments, the microfluidic device may include an interface chip, and the flow controller may be configured to draw the blanking solution into a microfluidic channel of the interface chip via an inlet port of the interface chip, wherein the blanking solution drawn into the microfluidic channel of the reaction chip of the microfluidic device to build the blanking slug is drawn from the microfluidic channel of the interface chip, and draw the sample solution into the microfluidic channel of the interface chip via the inlet port of the interface chip. The sample solution drawn into the microfluidic channel of the reaction chip of the microfluidic device to build the sample slug may be drawn from the microfluidic channel of the interface chip.

In some embodiments, the microfluidic device may include a T-junction. The flow controller may be configured to: in drawing the blanking solution into the microfluidic channel of the reaction chip of the microfluidic device, fill the T-junction with the blanking solution from the microfluidic channel of the interface chip and draw the blanking solution into the microfluidic channel of the reaction chip from the T-junction; and, in drawing the sample solution into the microfluidic channel of the reaction chip of the microfluidic device, fill the T-junction with the sample solution from the microfluidic channel of the interface chip and draw the sample solution into the microfluidic channel of the reaction chip from the T-junction. The detection system may be configured to determine whether the blanking solution has filled the T-junction by detecting whether a leading edge of the blanking solution has reached a region of interest in the interface chip of the microfluidic device. The detection system may be configured to determine whether the sample solution has filled the T-junction by detecting whether a trailing edge of the blanking solution has reached the region of interest in the interface chip of the microfluidic device.

In still another aspect, the present invention provides a microfluidic device including at least one microfluidic channel, a thermal element, a controller, and detector. The at least one microfluidic channel may be configured to receive a carrier fluid and a sample slug. The sample slug may contain polymerase chain reaction (PCR) reagents. The thermal element may be in thermal communication with a first zone of the at least one microfluidic channel. The controller may be configured to control the thermal element to thermocycle the sample slug in the microfluidic channel to perform a PCR reaction followed by a high resolution thermal melt (HRTM) in the first zone of the microfluidic channel. The detector may be configured to detect a fluorescent signal from the sample slug located in the microfluidic channel. The controller may be configured to independently adjust operating parameters of the PCR reaction for consecutive slugs.

In some embodiments, a length of the sample slug may limit the at least one microfluidic channel to having a single sample slug. Adjusting operating parameters associated with the PCR reaction for each sample slug may include optimizing a PCR amplification profile and a ramp temperature profile of the melt analysis based upon the fluorescent signal. The controller may be configured to stop the sample slug in the microfluidic channel for performing the PCR reaction and the melt analysis. The controller may be configured to perform the PCR reaction and the melt analysis on a flowing sample slug.

In some embodiments, the microfluidic channel may include the first zone and a second zone, the first zone may be in thermal communication with the thermal element, and the second zone may be outside the first zone. The controller may be configured to control a position of the sample slug by controlling a position of a leading edge of the sample slug located in the second zone of the microfluidic channel. The length of the sample slug may fill the microfluidic channel with a single sample slug and a single carrier fluid slug.

In yet another aspect, the present invention provides a method for processing a sample slug in a microfluidic device. The method may include: loading a sample slug containing polymerase chain reaction (PCR) reagents and followed by a carrier fluid slug into at least one microfluidic channel; thermocycling the sample slug in the microfluidic channel to perform a PCR reaction, wherein the PCR reaction is performed in a first zone of the microfluidic channel; following thermocycling, performing a melt analysis, wherein the melt analysis is performed in the first zone of the microfluidic channel; detecting a fluorescent signal from the sample slug in the microfluidic channel; and independently adjusting operating parameters of the PCR reaction for consecutive sample slugs.

In some embodiments, a length of the sample slug may limit the at least one microfluidic channel to having a single sample slug.

In another aspect, the present invention provides a system including at least one microfluidic channel to perform a polymerase chain reaction (PCR) followed by a melt analysis on a sample slug containing PCR reagents. The PCR reaction and the melt analysis may be performed in a first zone of the at least one microfluidic channel. An image sensor may have a first image sensor region having a first field of view and a second image sensor region having a second field of view. The second field of view may be different than the first field of view. At least a portion of the first zone may be within the first field of view to detect a signal associated with the PCR reaction and the melt analysis. A leading edge of the sample slug bordering with a carrier fluid slug may be within the second field of view during the PCR reaction and the melt analysis.

In some embodiments, the first field of view may detect the signal from a center of the first zone.

In still another aspect, the present invention provides a microfluidic device comprising: at least one microfluidic channel to receive a sample slug containing polymerase chain reaction (PCR) reagents; and a heating system in thermal communication with a first region of the microfluidic channel to thermocycle the sample slug in the first region of the microfluidic channel to perform a PCR reaction and to ramp the temperature of the sample slug in the first region of the microfluidic channel to perform a melt analysis. The first region of each microfluidic channel may be limited to having a single sample slug at any point in time during the PCR reaction and the melt analysis. A thermocycling profile and operating parameters of the PCR reaction may be individually adjusted for each sample slug based upon a fluorescent signal resulting from the thermocycling.

The above and other aspects and features of the present invention, as well as the structure and application of various embodiments of the present invention, are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF THE PREFERRED EMBODIMENTS

Figure 1:
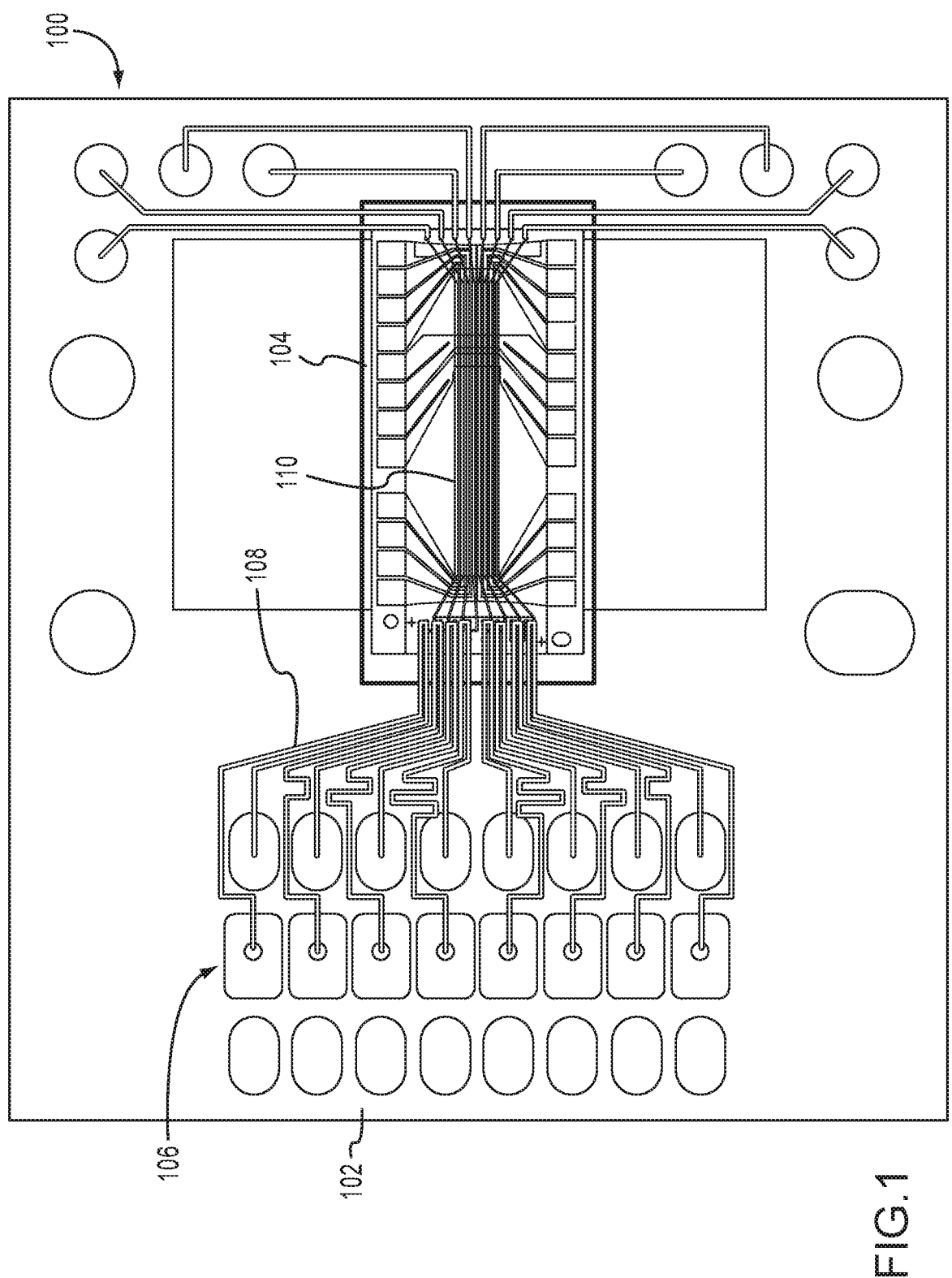
FIG. 1 illustrates a microfluidic device embodying aspects of the present invention.

FIG. 1 illustrates a microfluidic device 100 embodying aspects of the present invention. In some embodiments, microfluidic device 100 may include an interface chip 102 and a reaction chip 104. The interface chip 102 may include one or more access tubes (e.g., capillary tubes or other tubes) or wells 106 that allow different solutions (i.e., mixtures or fluids) to be entered into the microfluidic device 100 in series. The interface chip 102 may include one or more microfluidic channels 108. The microfluidic channels 108 of the interface chip 102 may be connected to the access tubes or wells 106. In some embodiments, the reaction chip 104 may carry out reaction chemistry, such as PCR polymerase chain reaction (PCR) amplification and thermal melting. The reaction chip 104 may include one or more microfluidic channels 110.

Figure 2:
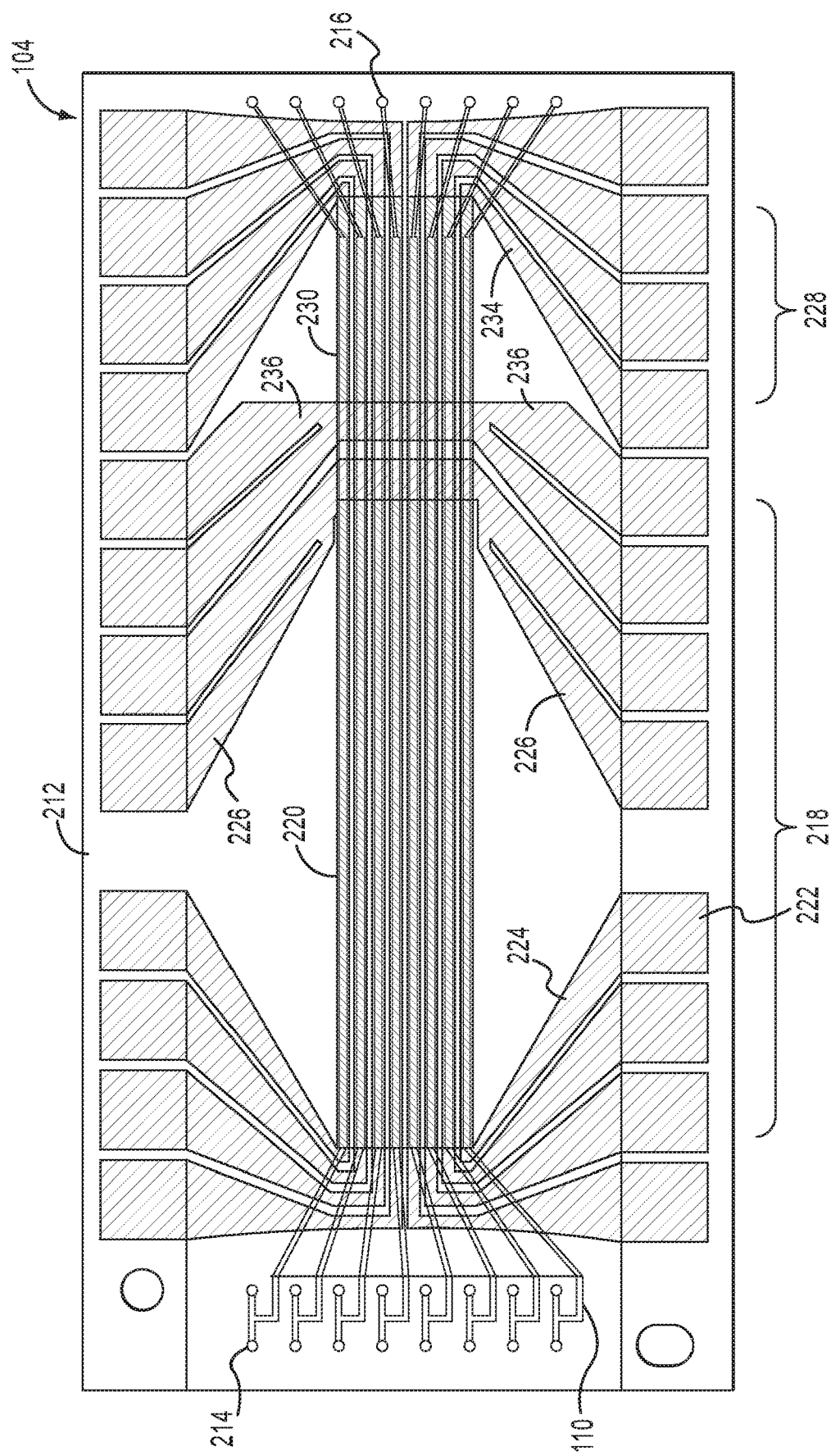
FIG. 2 illustrates a reaction chip embodying aspects of the present invention.

FIG. 2 illustrates a reaction chip 104 according to one non-limiting embodiment. As illustrated in FIG. 2, the reaction chip 104 includes several (e.g., eight) microfluidic channels 110 extending across a substrate 212. In other embodiments, more or fewer than the illustrated eight microfluidic channels may be used. Each microfluidic channel 110 of the reaction chip 104 may include one or more ports 214 (the illustrated embodiment shows two ports 214 per channel 110) and one or more outlet ports 216 (the illustrated embodiment shows one outlet port 216 per channel 110). In a non-limiting embodiment having two ports 214 per channel, fluids/solutions may be provided to a T-junction (e.g., T-junction 477 of FIG. 4) of the reaction chip 104 through one port 214 (e.g., the left side port 214), and fluids/solutions from the T-junction may exit the reaction chip 104 through the other port 214 (e.g., the right side port 214). For instance, in one embodiment, the ports 214 may be used to load fluid/solution onto the reaction chip 104 from an attachable interface chip or cartridge, and outlet port(s) 216 may be used to controllably pull the loaded fluid/solution through one or more microfluidic channels 110 of the reaction chip 104.

In some embodiments, as illustrated in FIG. 2, each microfluidic channel 110 may pass through a thermal zone 218 (i.e., a first zone) of the reaction chip 104. One or more heating elements 220 (i.e., one or more thermal elements or heaters) may be associated with the thermal zone 218. In some embodiments, a single heating element 220 may heat all microfluidic channels 110 that pass through the thermal zone 218. In other embodiments, a plurality of individually controlled heating elements 220 may be associated with the thermal zone 218, and each heating element 220 may heat a plurality of the microfluidic channels 110 that pass through the thermal zone 218. For example, in a reaction chip 104 having eight microfluidic channels 110, a first heating element 220 may heat four of the microfluidic channels 110 in the thermal zone 218, and a second heating element 220 may heat the other four microfluidic channels 110 in the thermal zone 218. In still other embodiments, such as the embodiment illustrated in FIG. 2, a plurality of individually controlled heating elements 220 may be associated with the thermal zone 218, and each heating element 220 may heat an associated one of the microfluidic channels 110 that pass through the thermal zone 218.

In some embodiments, the one or more heating elements 220 may be in the form of thin film resistive heaters associated with the microfluidic channels 110 in the thermal zone 218. For example, in one non-limiting embodiment, the one or more heating elements 220 may be platinum thin film resistive heaters. The resistances of the thin film resistive heaters may be measured in order to control the respective temperatures of the thin film resistive heaters.

In some embodiments, the reaction chip 104 may include heater electrodes 222 connected to the heating elements 220.

In non-limiting embodiments, heater electrodes 222 may include thermal zone leads 224 and one or more thermal zone common leads 226. According to one embodiment, a separate thermal zone lead 224 may be connected to each of the heating elements 220.

In some embodiments, as illustrated in FIG. 2, each microfluidic channel 110 may pass through a second zone 228 of the reaction chip 104. In some non-limiting embodiments, the second zone 228 is an unheated zone. In some embodiments, no heating elements are associated with the second zone 228. However, this is not required, and, in some alternative embodiments, one or more heating elements 230 may be associated with the second zone 228. In some embodiments having one or more heating elements 230 associated with the second zone 228, the heating elements 230 may not be used to heat the microfluidic channels 110. That is, even though one or more heating elements 230 may be associated with the second zone 228, in some embodiments, the heating elements 230 may remain off and may not be controlled to provide heat. In an alternative embodiment, the reaction chip 104 may have only a single zone 218 that may be associated with one or more heating elements 220.

In one non-limiting embodiment, as illustrated in FIG. 2, a plurality of individually controlled heating elements 230 may be associated with the second zone 228, and each heating element 230 may be capable of heating an associated one of the microfluidic channels 110 that pass through the second zone 228 (even though the heating elements 230 may not be controlled to do so). However, other configurations may be used (e.g., a single heating element 230 may be capable of heating all of the microfluidic channels 110 passing through the second zone 228, plural heating elements 230 may each be capable of heating plural microfluidic channels 110 passing through the second zone 228).

In some embodiments, the one or more heating elements 230 may be in the form of thin film resistive heaters associated with the microfluidic channels 222 in the second zone 228. In non-limiting embodiments, the heater electrodes 110 may include second zone leads 234 and one or more second zone common leads 236. As illustrated in FIG. 2, in some embodiments, a separate second zone lead 234 may be connected to each of the heating elements 230.

Figure 3:
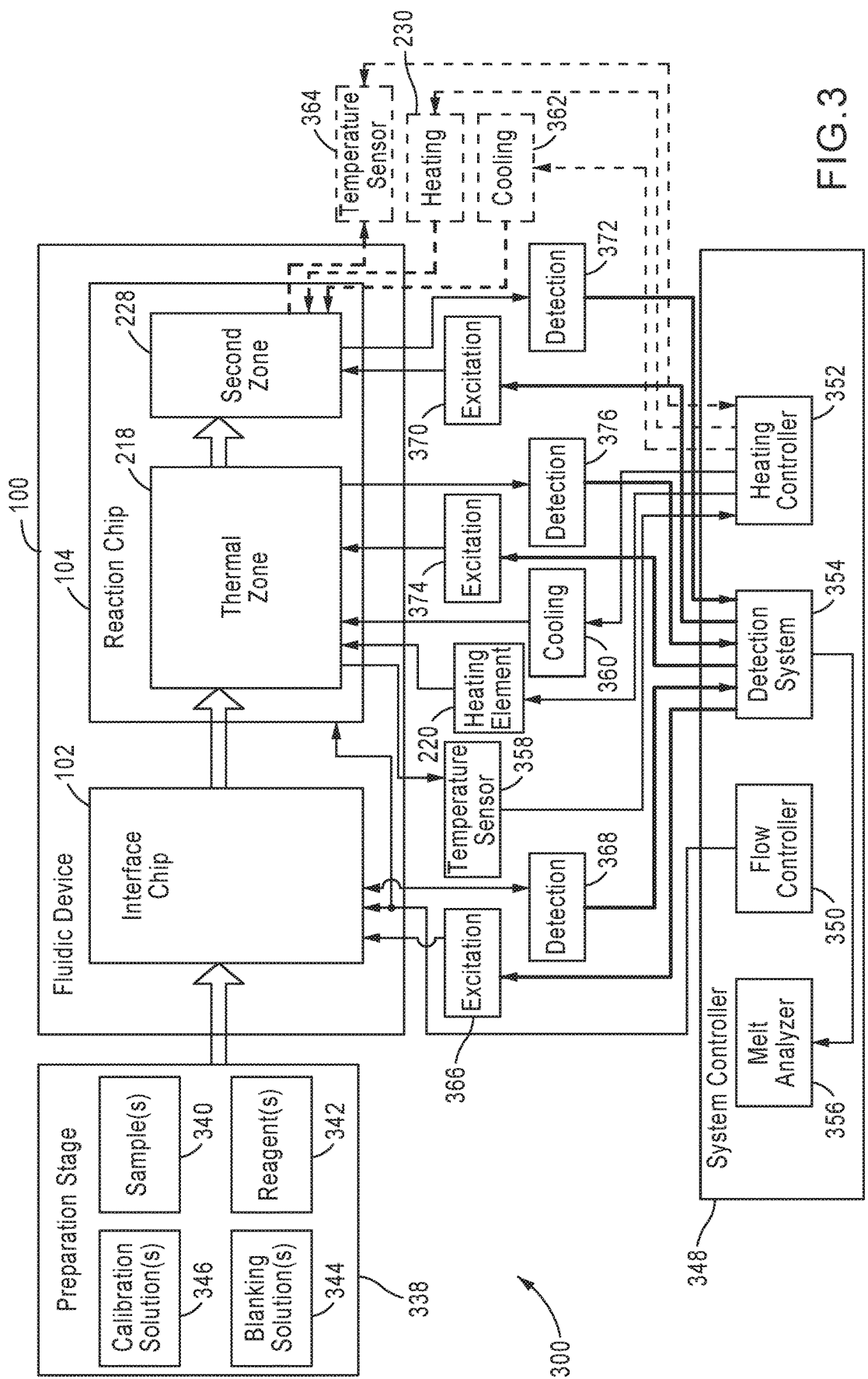
FIG. 3 is a functional block diagram of a microfluidic reaction system for using a microfluidic device embodying aspects of the present invention.

FIG. 3 illustrates a functional block diagram of a microfluidic reaction system 300 for using a microfluidic device 100, in accordance with one embodiment. In some embodiments, the microfluidic reaction system 300 may be a single slug system implementing a single slug approach.

In some embodiments, the microfluidic reaction system 300 may include a preparation stage 338 (e.g., a pipettor system). In one non-limiting embodiment, the preparation stage 338 may comprise appropriate devices (e.g., PCR robots) for preparing one or more sample solutions and appropriate devices (e.g., blanking robots) for preparing one or more blanking solutions. For instance, as illustrated in FIG. 3, the preparation stage 338 may include one or more samples 340 and one or more reagents 342 and may prepare a sample solution by mixing a sample 340 with one or more reagents 342. In some non-limiting embodiments, the preparation stage 338 may include the micropipette 700 or 700' described with references to FIGS. 7A and 7B, respectively, of U.S. Patent Application Publication No. 2012/0058519, which is incorporated by reference herein in its entirety, and preparation of the sample solutions may be as described with reference to FIG. 6 of U.S. Patent Application Publication No. 2012/0058519. In some non-limiting embodiments, the sample solutions may contain an intercalating dye, such as, for example, LCGreen+ dye.

In some embodiments, the preparation stage 338 may input one or more fluids into the microfluidic device 100. The fluids input by the preparation stage 338 may include one or more sample solutions, one or more blanking solutions 344 (e.g., spacer solutions), and/or one or more calibration solutions 346. A calibration solution 346 may include a known sample having a known melting temperature. In some non-limiting embodiments, the calibration solutions may include a first calibration solution having a first sample having a first melting temperature and a second calibration solution having a second sample having a second melting temperature. In some non-limiting embodiments, one or more of the calibration solutions 364 may be a compound calibrator, such as, for example a compound calibrator as described in U.S. Patent Application Publication No. 2012/0051390, which is incorporated by reference herein in its entirety. In some non-limiting embodiments, one or more of the calibration solutions 364 may include one or more amplicons having a known or expected thermal melting temperature, such as, for example, one or more amplicons described in U.S. Patent Application Publication No. 2012/0178077, which is incorporated by reference herein in its entirety.

In some embodiments, fluids from the preparation stage 338 may enter into the microfluidic channels 108 of the interface chip 102 of the microfluidic device 100 via the access tubes or wells 106 of the interface chip 102. The fluids from the microfluidic channels 108 of the interface chip 102 may enter the microfluidic channels 110 of the reaction chip 104 via ports 214 of the reaction chip 104. In the thermal zone 218 of the reaction chip, fluids in the microfluidic channels 110 of the reaction chip 104 may be subjected to thermal cycling (i.e., temperature cycling) for PCR followed by a thermal ramp (i.e., temperature ramp) for melt data acquisition.

In some embodiments, the microfluidic reaction system 300 may include a system controller 348. The system controller 348 may include a flow controller 350, heating controller 352, detection system 354, and/or melt analyzer 356. The flow controller 350, heating controller 352, detection system 354, and/or melt analyzer 356 may each or collectively be a programmed computer having a processor and memory, an application specific integrated circuit, or other digital and/or analog control circuit.

The flow controller 350 may control flow of fluids through the microfluidic channels 108 of interface chip 102 and the microfluidic channels 110 of reaction chip 104. In some embodiments, the flow controller 350 may control pressures in the channels of the microfluidic device 100 via one or more pumps. In some embodiments, the flow controller 350 may use feedback regarding the positions of fluid in the microfluidic device 100. In some embodiments, the flow controller 350 may be a proportional-integral-derivative (PID) controller.

The heating controller 352 (i.e., thermal controller) may control heating of one or more heating elements 220 associated with the thermal zone 218. In non-limiting embodiments, control of the heating elements 220 may be based on temperatures determined by one or more temperature sensors 358 (such as, for example, RTD or thin-film thermistors or thin-film thermocouple thermometers). In this way, the temperatures of one or more channels 110 in the thermal zone 218 may be maintained at a desired temperature, cycled through desired temperatures, and/or ramped according to one or more temperature sequences or profiles. However, in some embodiments, such as where the heating elements 220 are thin film heaters, the heating elements 220 may provide the function of the temperature sensors 358. In some embodiments of the present invention, the thermal zone 218 may also be cooled by one or more cooling devices 360 (for example, to quickly bring the temperature of a channel 110 in the thermal zone 218 from 95° C. down to 55° C.), which may also be controlled by the heating controller 352. In one embodiment, a cooling device 360 could be a Peltier device, heat sink, or forced convection air cooled device, for example.

In some embodiments, the heating controller 352 may be configured to cause the one or more heating elements 220 to heat the thermal zone 218 of the reaction chip 104 to cycle the temperature of the thermal zone 218 according to a PCR amplification profile. In some embodiments, the heating controller 352 may be configured to, subsequent to the heating according to the PCR amplification profile, cause the one or more heating elements 220 to ramp the temperature of the thermal zone 218 of the reaction chip 104 according to a temperature ramp profile. In some non-limiting embodiments, the heating controller 352 may switch heater control modes according to a script or similar order to go between PCR heating and thermal melt heating in the same zone (e.g., thermal zone 218). In one non-limiting embodiment, the heating controller 352 may switch modes to allow for a denature/renature step between the PCR and thermal melt heating modes.

In some non-limiting embodiments, the heating controller 352 (i.e., thermal controller) may have the capability to control the temperature in the second zone 228. In these embodiments, the microfluidic reaction system 300 may include one or more heating elements 230, one or more cooling elements 362, and one or more temperature sensors 364 to raise, lower, and detect the temperature of one or more channels 110 in the second zone 228, respectively. However, this is not necessary, and, in some embodiments, the microfluidic reaction system 300 may not have a heating element 230, cooling element 362, or temperature sensors 364 associated with the second zone 228. Also, as noted above, even in some embodiments where the heating controller 352 may have the capability to control the temperature in the second zone 228, the heating controller 352 may not control the heating element 230 to heat to the channels 110 in the second zone 228.

The detection system 354 may monitor flow in the channels 108 of interface chip 102, monitor flow in the channels 110 of reaction chip 104, and/or measure fluorescence from the reaction chip 104 during PCR amplification and/or melt data acquisition. In some embodiments where the detection system 354 monitors flow in the channels 108 of interface chip 102 and/or the channels 110 of reaction chip 104, the detection system 354 may provide feedback to the flow controller 350. Also, in some embodiments where the detection system 354 monitors flow in the channels 108 of interface chip 102 and/or the channels 110 of reaction chip 104, the detection system 354 may include a fluorescent dye imaging and tracking system, which may include features such as those described in U.S. Pat. No. 7,629,124 and U.S. Patent Application No. 2012/0058460, which are incorporated herein by reference in their entirety.

In some non-limiting embodiments, as illustrated in FIG. 3, the detection system 354 may control an interface excitation device 366 to excite a fluorescent dye (e.g., Alexa647) in fluid (e.g., blanking solution) in the channels 108 of the interface chip 102 and receive a signal indicative of fluorescent light emitted from the fluid in the channels 108 of the interface chip 102 and detected by an interface detection device 368. Similarly, the detection system 354 may control a reaction flow excitation device 370 to excite a fluorescent dye in fluid in one or more channels 110 in the second zone 228 of the reaction chip 104 and receive a signal indicative of fluorescent light emitted from the fluid in the one or more channels 110 in the second zone 228 of the reaction chip 104 and detected by reaction flow detection device 372.

In some embodiments where the detection system 354 measures fluorescence of the reaction chip 104 during PCR amplification and/or melt data acquisition, the detection system 354 may control a thermal zone excitation device 374 to excite a fluorescent dye in fluid in one or more channels 110 in the thermal zone 218 of the reaction chip 104 and receive a signal indicative of fluorescent light emitted from the fluid in the one or more channels 110 in the thermal zone 218 of the reaction chip 104 and detected by thermal zone detection device 376. In some non-limiting embodiments, the thermal zone excitation device may include one or more light emitting diodes (LEDs) (e.g., blue LEDs). Further, in one embodiment, the thermal zone excitation device 374 may be capable of being operated in one or more modes (e.g., a low power/intensity mode and a high power/intensity mode).

In some non-limiting embodiments, one or more of the detection devices 368, 372, and 376 may be part of an image sensor system. The image sensor system may have one or more cameras. In some embodiments, the image sensor system may be as described in U.S. Patent Application Publication No. 2008/0003593 or U.S. Pat. No. 7,629,124, which are incorporated herein by reference in their entirety. In embodiments having an image sensor system, the detection controller 354 may be an imaging system controller. Although excitation devices 366, 370, and 374 and detection devices 368, 372, and 376 are illustrated as separate devices in FIG. 3, in some non-limiting embodiments, excitation devices 366, 370, and 374 and detection devices 368, 372, and 376 may all be part of a single excitation/detection device, which in one embodiment may only view one of the interface chip 102, thermal zone 218, and second zone 228 at any given time and may be configured to switch between views during processing.

Figure 10:
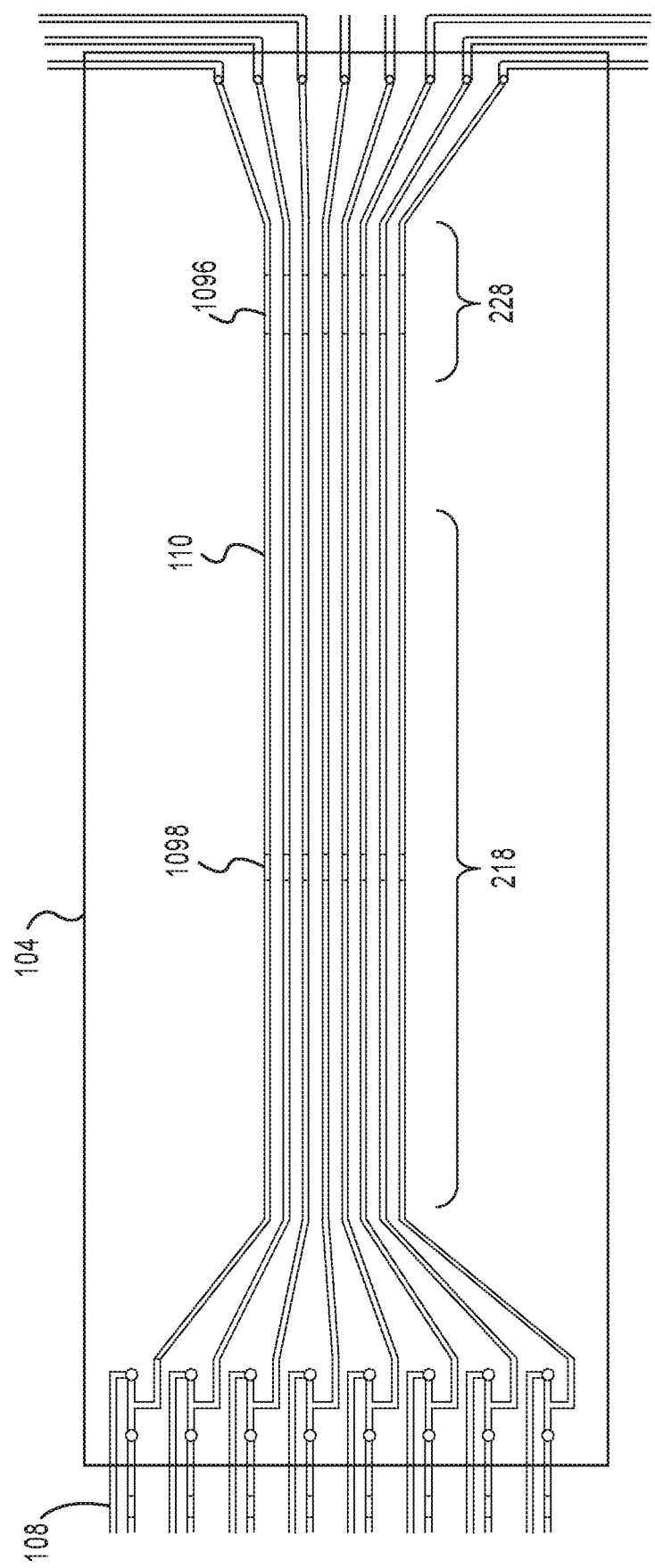
FIG. 10 illustrates regions of interest according to aspects of the present invention.

In some embodiments, one or more of the detection devices 368, 372, and 376 may include an image sensor (e.g., a camera) having a first image sensor region (e.g., thermal region 218) having a first field of view, which may include regions of interest 1098 and a second image sensor region (e.g., second region 228) having a second field of view, which may include regions of interest 1096 (see FIG. 10). In some embodiments, the image sensor may also have a third image sensor region (e.g., an interface chip region) having a third image sensor region, which may include regions of interest 491 (see FIGS. 4 and 10). In operation, the image sensor may switch between the fields of view and capture images of the image sensor regions (or portions thereof). The detection system 354 may be capable of controlling the image system in different modes. For instance, in a melt mode, the image system may capture high speed images and store them in a melt data buffer of the system 300.

In some embodiments, the system 300 may include a melt analyzer 356 capable of performing a melt analysis to identify the melting temperature of a nucleic acid in the sample slug based on the fluorescence from the portion of the sample slug in the thermal zone measured by the detection system 354 during melt data acquisition. In some embodiments, the melt analyzer 300 may be a computer having a processor and memory that is programmed to perform the melt analysis. However, in alternative embodiments, the melt analyzer 356 may be an application specific integrated circuit or other digital and/or analog control circuit that is configured to perform the melt analysis.

Figure 4:
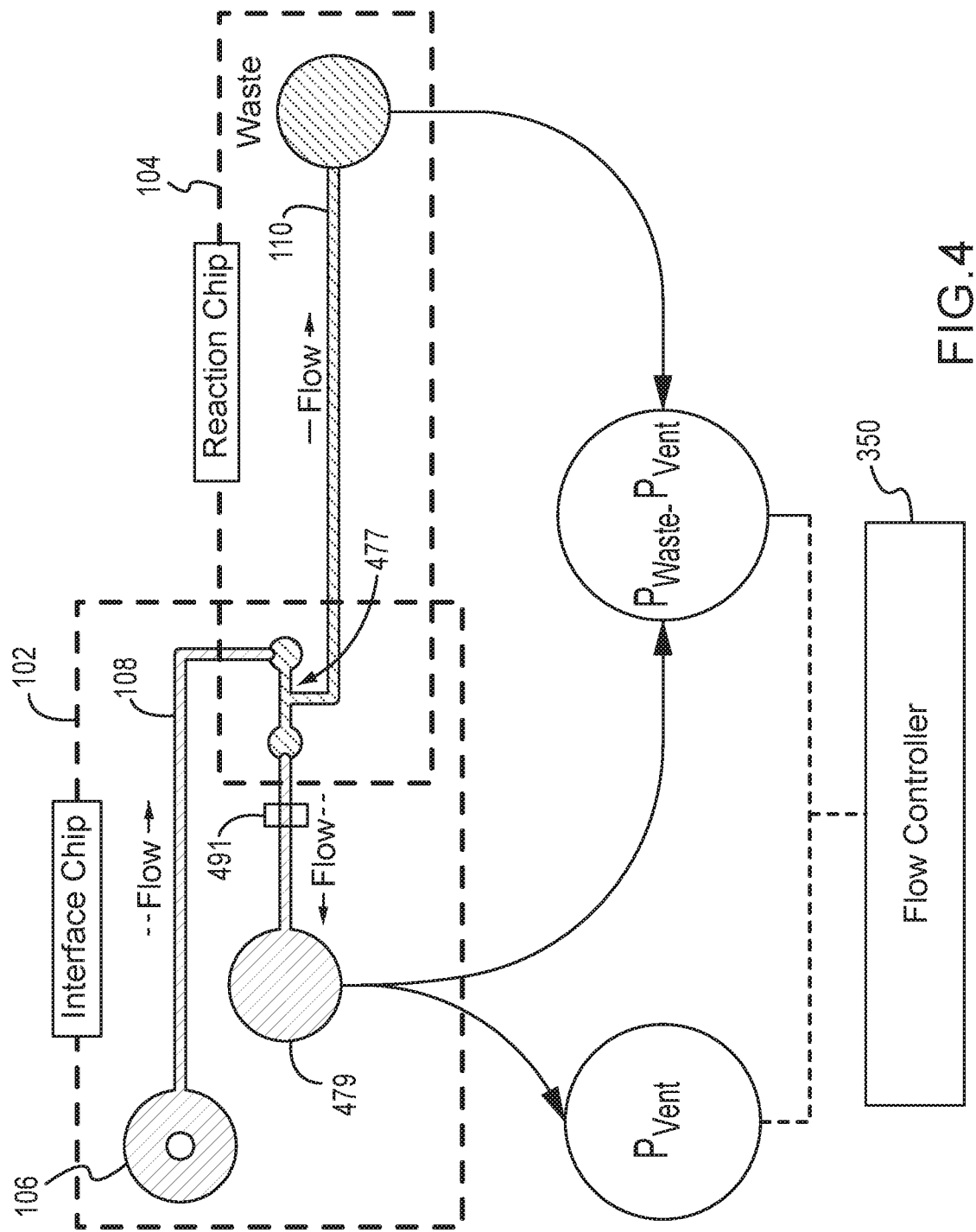
FIG. 4 illustrates a T-junction of a microfluidic device embodying aspects of the present invention.

As illustrated in FIG. 4, in some embodiments, the microfluidic device 100 may include one or more T-junctions 477. In some embodiments, each microfluidic channel 110 of the reaction chip 104 may receive fluid from a microfluidic channel 108 of the interface chip 102 through the T-junction 477. In some non-limiting embodiments, a channel 108 of the interface chip 102 may provide fluid to a T-junction 477, and a channel 108 of the interface chip 102 may provide fluid from the T-junction 477 to a vent well 479. In some embodiments, the detection system 354 may monitor flow in a channel 108 of the interface chip 102 by determining whether a fluid has reached an interface flow monitoring region and, thus, has filled the T-junction 477. In the embodiment illustrated in FIG. 4, the T-junction 477 is located in reaction chip 104 of the microfluidic device 100. However, this is not necessary, and, in alternative embodiments, the T-junction 477 may be located in interface chip 102 of the microfluidic device 100.

In some non-limiting embodiments, the system controller 348 may cause the preparation stage 338 to provide a drop of fluid on the access tubes or wells 106. The flow controller 350 may set a negative pressure at a vent well to draw the fluid into a microfluidic channel 108 of the interface chip 102, through a T-junction 477, and then to the vent well 479. After the fluid has passed through (i.e., filled) the T-junction 477, the flow controller 350 may stop fluid flow into the channel 108 of the interface chip 102 and then draw the fluid from the T-junction 477 into the channel 110 of the reaction chip 104. Once the fluid slug has reached the desired region or location in the channel 110 of the reaction chip 104, the flow controller 350 may cause the fluid flow to stop in the reaction chip 104. The system controller 348 may then cause the preparation stage 338 to place a new drop of fluid on the access tubes or wells 106. The system controller 348 can then cause the process to begin and then loop until all desired slugs have been created.

In some embodiments, the T-junction between an interface chip and a reaction chip can be utilized to create alternating slugs of multiple fluids (e.g., blanking solution(s), sample solution(s), and/or calibration solution(s)) while decreasing the amount of diffusion between the slugs, as is described in U.S. Patent Application Publication No. 2011/0091877, which is incorporated by reference herein in its entirety.

In some embodiments, the devices and systems described above may implement a single slug approach to performing PCR amplification and melt data acquisition. In some embodiments utilizing the single slug approach, no more than a one slug per microfluidic channel 110 of the reaction chip 104 may be present in the thermal zone 218, and the thermal zone 218 may be used for both PCR amplification and melt data acquisition. That is, in some embodiments utilizing the single slug approach, a sample/test slug need not be moved from the thermal zone 218 in which temperature cycling was performed to a different thermal zone for a temperature ramp. Further, in some embodiments utilizing the single slug approach, the need to create short slugs as in the multi-slug approach is eliminated, and the reaction chip 104 may be substantially filled with one sample solution at a time. The single slug approach may break the coupling between events present in the multi-slug approach and enable processing of events to be controlled independently. For example, TABLE 2 below illustrates the events occurring during steps of an exemplary basic single slug processing sequence in a single slug system having a microfluidic device with an interface chip (K-Chip) and a reaction chip (U-chip). In TABLE 2 below, important events are shown in bold.

TABLE 2

| Step # | K-Chip Flow Events | U-Chip Flow Events | Zone 1 Events | Exemplary Time (s) |
|---|---|---|---|---|
| 1 | — | Pull In Blanking Slug | — | 40 |
| 2 | Load Sample Solution | Hold Blanking Slug | — | 40 |
| 3 | — | Pull In Sample Slug | — | 40 |
| 4 | — | Hold Sample Slug | Hot Start (Optional) | 30 |
| 5 | Load Blanking Solution | Hold Sample Slug | PCR | 400 |
| 6 | — | Hold Sample Slug | Melt | 30 |

As shown in TABLE 2, the single slug approach may break flow, PCR, and melt events into different steps so that they can be controlled independently without the need to compromise on one to satisfy another. In other words, one event may essentially drive each step. As shown in TABLE 2, step 5 of the exemplary basic single slug processing sequence may include both the "Load Blanking Solution" interface chip flow event and the reaction chip thermal zone (Zone 1) event "PCR." In practice, the PCR event may last much longer than the "Load Blanking Solution" interface chip flow event. As a result, including the "Load Blanking Solution" interface chip flow event and the PCR event in the same step may not require either step to be compromised and may simply save time (e.g., approximately 40 s) in setting up the next sample slug. However, in an alternative embodiment, the "Load Blanking Solution" interface chip flow event could occur in its own step (e.g., following the melt event step and while the reaction chip holds the sample slug). Also, exemplary times are given in TABLE 2, but, in other embodiments, different step times may be used.

Independent control of the processing events may allow independent optimization of each event. For example, if thermal cycling of a sample slug for PCR needs more time, then additional time can be added to the thermal cycling of the sample without affecting flow. Also, in some embodiments, flow steps may be completed as fast as possible without regard to how much time is required for PCR.

In some non-limiting embodiments, the flow controller 350 in the single slug system 300 may use feedback (e.g., image based feedback) to drive peristaltic pumps connected to waste ports of the microfluidic device 100. In some embodiments, the feedback based control performed by the flow controller 350 may alternate between active control of the leading and trailing edges of blanking slugs, such as blanking slugs 878 shown in FIGS. 8B-8L. In some embodiments, the one or more blanking solutions 344 used to form the blanking slugs may contain a dye that allows both sample and blanking slugs to be controlled. In some embodiments, the blanking solution/slug dye may be a dye (e.g., Alexa647) that produces a red signal when excited. However, this is not required, and, in alternative embodiments, other dyes, which may produce a signal have a color other than red, may be used.

In some embodiments, the detection system 354 may determine the current position of a slug using edge detection (i.e., by looking for gradients in the red signal). The edge detection may be performed in real time by a controller such as LabView, which may be running with a process loop at, for example, 1 Hz. In some embodiments, the control edge (i.e., the leading or trailing edge being tracked) may be located in the second zone 228 (e.g., an unheated area) of the reaction chip 104. For instance, in one non-limiting embodiment, the second zone 228 may be the region of a reaction chip 104 that would be used as a data acquisition zone under the multi-slug approach. However, this is not required. In some embodiments, using a zone that is unheated for flow control may eliminate problems associated with dye (e.g., Alexa647) intensity changes due to thermal cycling.

In some embodiments, based on feedback from the detection system 354, the flow controller 350 may control the leading edge of a blanking slug 878 to a blanking slug building target region, such as the region 880 shown in FIGS. 8A-8L. See FIGS. 8B, 8C, 8F, 8G, 8J, and 8K. In some embodiments, as illustrated in FIGS. 8A-8L, the blanking slug building target region may be within the second zone 228 of the reaction chip 104. In some non-limiting embodiments, based on feedback from the detection system 354, the flow controller 350 may further control the leading edge of a blanking slug 878 to a control point within the blanking slug building target region. For instance, in one non-limiting embodiment, the control point may be in the middle of the region 880.

In some embodiments, based on feedback from the detection system 354, the flow controller 350 may control the trailing edge of a blanking slug 878 to a sample slug building target region, such as the region 880 shown in FIGS. 8A-8L. See FIGS. 8D, 8E, 8H, 8I, 8L. In some embodiments, as illustrated in FIGS. 8A-8L, the sample slug building target region may be within the second zone 228 of the reaction chip 104. In some non-limiting embodiments, based on feedback from the detection system 354, the flow controller 350 may further control the trailing edge of a blanking slug 878 to a control point within the sample slug building target region. For instance, in one non-limiting embodiment, the control point may be in the middle of the region 880. In some embodiments, the blanking slug building target region may be the same region as the sample slug building target region. However, this is not required, and, in other embodiments, the blanking slug building target region and the sample slug building target region may be different regions.

By holding the trailing edge of a blanking slug 878 in the sample slug building target region (e.g., slug building target region 880), the flow controller 350 may hold a sample slug 890 that follows the blanking slug 878 in a microfluidic channel 110 of the reaction chip 104 in place for PCR amplification and melt data acquisition in the thermal zone 218 of the reaction chip 104. See, e.g., FIGS. 8H and 8L.

In some embodiments, during thermal cycling in the thermal zone 218 for PCR amplification, the flow controller 350 of the single slug system 300 may be operated in one of three flow modes: (1) stopped flow mode, (2) continuous flow mode, and (3) intermittent motion mode.

In stopped flow mode, the flow controller 350 may hold a single sample slug in a fixed position for the duration of PCR amplification and melt data acquisition. Operation in stopped flow mode allows complete flexibility in the choice of PCR amplification and temperature ramp temperature profiles. In other words, with the stopped flow mode, the temperatures, hold times, ramp rates, number of cycles, and/or other parameters of the temperature profile may be freely selected. Available options when using the stopped flow mode may include, for example, hot-start PCR amplification, a denature-renature step before melting, slower melt times, and/or multiple melts times. Furthermore, unlike with the multi-slug approach, temperature profiles may be selected without regard to whether heating according to the temperature profile will complete within the requirements of the slug train timing.

In continuous flow mode, the flow controller 350 may slowly draw a single slug across the single thermal zone 218 while the PCR temperature cycling is being carried out, and, then, a temperature ramp could be done in the same thermal zone 218 once PCR is complete. For this mode, the flow rate is preferably sufficiently low to ensure that the sample remains in the thermal zone 218 for the entirety of PCR amplification and melt data acquisition. In fluid mechanics, these very slow flows are sometimes called creeping flows. With sufficiently low flow rates the dispersion of chemical species may be negligible.

In intermittent motion mode, the flow controller 350 may control flow in the one or more channels 110 of the reaction chip 104 so that the single slug is neither (a) completely stopped during the entirety of PCR temperature cycling and temperature ramping nor (b) always moving. In some intermittent motion mode embodiments, the slug may be moved for only part of a portion of the time before and/or after being stopped for a period of time. However, in alternative intermittent motion mode embodiments, the slug may be moved back and forth. For example, the flow controller 350 may control flow in the manner described in U.S. Provisional Patent Application No. 61/788,729, which was filed Mar. 15, 2013, is entitled "Method for Enhancement of Polymerase Chain Reaction Through Laminar Flow Mixing", and is incorporated by reference herein in its entirety.

In some single slug embodiments, flow rates used to move slugs through the cartridge may be easily customized to suit the needs of a particular device. For example, in a non-limiting embodiment, flow in a microfluidic channel 108 of the interface chip 102 through a T-junction 477 and to the vent may be open loop (i.e., no feedback control) or closed loop (i.e., feedback control).

In regard to flow rates in the interface chip 102 (a.k.a., K-chip), assuming that the microfluidic device 100 contains no tracking or blanking slug at start-up, the first flow may be open loop. See, e.g., FIG. 9A at step "K Blank Asp OL." For example, in one non-limiting embodiment, the open loop flow rate for the blanking solution may be 12 nL/s with 2 nL/s$^2$ ramps for a volume of 500 nL. Then, in some embodiments, with a blanking slug on the device to use for feedback control, different 'closed loop' flow rates may be used. For example, in one non-limiting embodiment, the open loop flow rate for all flows other than the first flow may be 15 nL/s with 2 nL/s$^2$ ramps for a volume of 500 nL.

In regard to flow rates in the reaction chip 104 (a.k.a., U-chip), flow through the thermal zone 218 in the one or more channels 110 of reaction chip 104 can also be open or closed loop. In some embodiments, it may be desirable to flush the reaction chip 104 to, for example, clean the reaction chip 104 or restart. For these flushes, an open loop flow rate may be used (e.g., 3 nL/s for 50 s) by applying a fixed pressure on the waste/outlet ports 216. For closed loop flows (i.e., flows where a blanking slug's position is used for feedback control), in some embodiments, a different set of flow rates may be used, and the flow controller 350, which may be a PID controller, may actively determine the appropriate set point (e.g., via PID control). In some non-limiting embodiments, the flow controller 350 may include certain 'gutter' values or anti-windup. In one non-limiting embodiment, the flow rate for test slugs may be 3 nL/s, and the flow rate for blanking slugs may be 3 nL/s.

In some embodiments, flow control in the single slug system 300 may include one or more of the methods to improve reliability (e.g., self-healing methods), such as, for example, those described in U.S. Provisional Patent Application No. 61/788,894, which was filed Mar. 15, 2013, is entitled "Flow Control in a Microchannel Network and Methods for Self Healing," and is incorporated by reference herein in its entirety. For example, some embodiments may include (i) smart turn off of flow in the interface chip 102 ("K-flow"), (ii) hydraulic calibration, and/or (iii) loss of control detection and retry.

In regard to smart turn off of flow in the interface chip 102 ("K-flow") embodiments, the detection system 354 may monitor a K-flow region of interest 491 in each of one or more channels 108 of the interface chip 102, and the flow controller 350 may turn off flow in the interface chip 102 based on feedback received from the detection system 354. For example, in one non-limiting embodiment, the flow controller 350 may ramp down K-flow in response to a detected signal from the K-flow region of interest 491 exceeding a threshold. In some embodiments, the K-flow region of interest 491 in a microfluidic channel 108 of the interface chip 102 may be upstream relative to the T-junction 477. In some embodiments, smart turn off of K-flow may be used in each K-flow step. However, in some alternative embodiments, smart turn off of K-flow may be limited to those steps when the upstream part of the interface chip 102 (relative to the T-junction 477) is visible (e.g., FIGS. 8A, 8C, 8G, 8K).

In regard to hydraulic calibration, in some embodiments, the detection system 354 may monitor one or more flow control regions of interest (ROIs) (e.g., K-flow ROI(s) 491 or U-flow ROI(s) 1096 in the slug building region 880 of the reaction chip 102), and the flow controller 350 may perform hydraulic calibration by appropriately adjusting the applied pressure differential based on the signals detected from the one or more monitored flow control ROIs.

In regard to loss of control detection and retry, in some embodiments, the detection system 354 may periodically monitor K-flow ROI(s) 491 and/or U-flow ROI(s) 1096 in the slug building region 880 of the reaction chip 102 to detect the presence of an expected slug. If the expected slug is not present, the flow controller 350 may flag the channel as lost. In some embodiments, a user may be given the option to manually retry or ignore. In some embodiments, the retry options may be turned off entirely or otherwise not available. However, in some embodiments, retry may be necessary for calibration because all heating elements 220 must be calibrated to run the microfluidic device 110 properly.

As illustrated in FIG. 10, in some embodiments, the single slug system 300 may use one or more regions of interest (ROIs) for flow control and/or analysis of biochemical products. In some embodiments, the single slug system 300 may have one or more interface chip flow control/slug control ROIs 491 (i.e., K-flow ROIs), one or more reaction chip flow control/slug control ROIs 1096 (i.e., U-flow ROIs), and one or more PCR/melt ROIs 1098. As illustrated in FIG. 10, in some embodiments, for each type of ROI, there may be an individual ROI of that type in each channel (i.e., one ROI for each channel).

In some embodiments, the PCR/melt ROIs 1098 may be used for real time PCR and/or melt data acquisition. In some embodiments, the PCR/melt ROIs 1098 may be small and may be well within the center of thermal zone 218. In one non-limiting embodiment, the PCR/melt ROIs 1098 are 110 um by 625 um. However, this is not required, and, in alternative embodiments, the PCR/melt ROIs 1098 may have different dimensions. In one non-limiting embodiment, the PCR/melt ROIs 1098 may be within the middle 50% of the thermal zone 218. The PCR/melt ROIs 1098 may be, for example, in the central region 882 shown in FIGS. 8A-8L.

In the system 300, in one embodiment, PCR amplification may be efficiently carried out in the PCR/melt ROIs 1098 of the thermal zone 218 because the sample in this portion of the thermal zone 218 is always in a temperature controlled section of the chip, and, as the calibration of the heating elements 220 may be performed in this portion of the thermal zone, the portion of the thermal zone 218 in the PCR/melt ROIs 1098 may be known to be accurately calibrated. Also, in some embodiments, the effective sample (i.e., the portion of the sample(s) at the PCR/melt ROI(s) 1098) does not undergo PCR when it is half in or half out of thermal zone 218 as is done in the multi-slug system.

In some embodiments, the reaction chip flow control/slug control ROIs 1096 (i.e., U-flow ROIs) may be used for closed loop reaction chip flow control. In one non-limiting embodiment, the U-flow ROIs 1096 are 110 um by 3 mm. However, this is not required, and, in alternative embodiments, the PCR/melt ROIs 1098 may have different dimensions.

In some embodiments, the interface chip flow control/slug control ROIs 491 (i.e., K-flow ROIs) may be used for self-healing flow control in the interface chip 102 (e.g., smart turn off of flow in the interface chip 102).

In some embodiments, thermal zone excitation device 374 may be used to excite dyes within slugs in the microfluidic channels 110 of the reaction chip 104 for real-time monitoring (e.g., for quantitative PCR). In some embodiments, additional illumination may be provided to improve the signal during melt. For example, in some non-limiting embodiments, the one or more microfluidic channels 110 the thermal zone 218 of the reaction chip 104 illuminated by thermal zone excitation device 374 with increased excitation light. In some non-limiting embodiments, a central region of the thermal zone 218 (e.g., the central 50% of the thermal zone 218) may be targeted with the increased excitation light.

The single slug system 300 is compatible with real time PCR, and, in some embodiments, the detection system 354 may collect real time PCR data by monitoring the fluorescence from the thermal zone 218 (e.g., from the PCR/melt ROIs 1098). In some embodiments, the same ROI 1098 may be used for both real-time PCR and melt data acquisition. However, this is not required, and, in some embodiments, different ROIs in the thermal zone 218 may be used for real-time PCR and melt data acquisition, respectively. In some embodiments, the detection system 354 may perform real-time PCR monitoring at a fixed rate (e.g., 1 Hz). During real-time PCR, thermal zone excitation device 374 (e.g., one or more LEDs) may be set at a lower current setting (than during melt data acquisition) to prevent photobleaching. In some non-limiting embodiments, to re-construct the real-time PCR curve, the highest fluorescence reading over each PCR cycle (e.g., a 10 or 20 s cycle) may be used as the intensity for that cycle. However, this is not required, and some alternative embodiments may use other fluorescence readings, such as, for example, the fluorescence at extension or the fluorescence during the lowest temperature step.

In some embodiments, the system 300 may perform calibration in slugs. In some embodiments, calibration may involve a melt of a known sample and use of the acquired melt data to determine heater/sensor calibration coefficients. In some non-limiting embodiments, following the calibration, the system 300 may use the same or a different known sample to verify the calibration. In other words, the system 300 may perform a melt to check calibration or "check melt." In one non-limiting embodiment, the entire calibration process may be automated and may take less than, for example, 10 minutes.

In some embodiments, the system 300 may perform a "hot start" PCR amplification by adding a hot start to the PCR amplification temperature profile. In a hot start PCR amplification, the system 300 may ramp the temperature of the sample slug in the thermal zone 218 to a hot start temperature, which may be user defined, and then held for a desired time to separate double-stranded human genomic DNA (initial denaturation) and activate the hot start enzyme.

Figure 5:
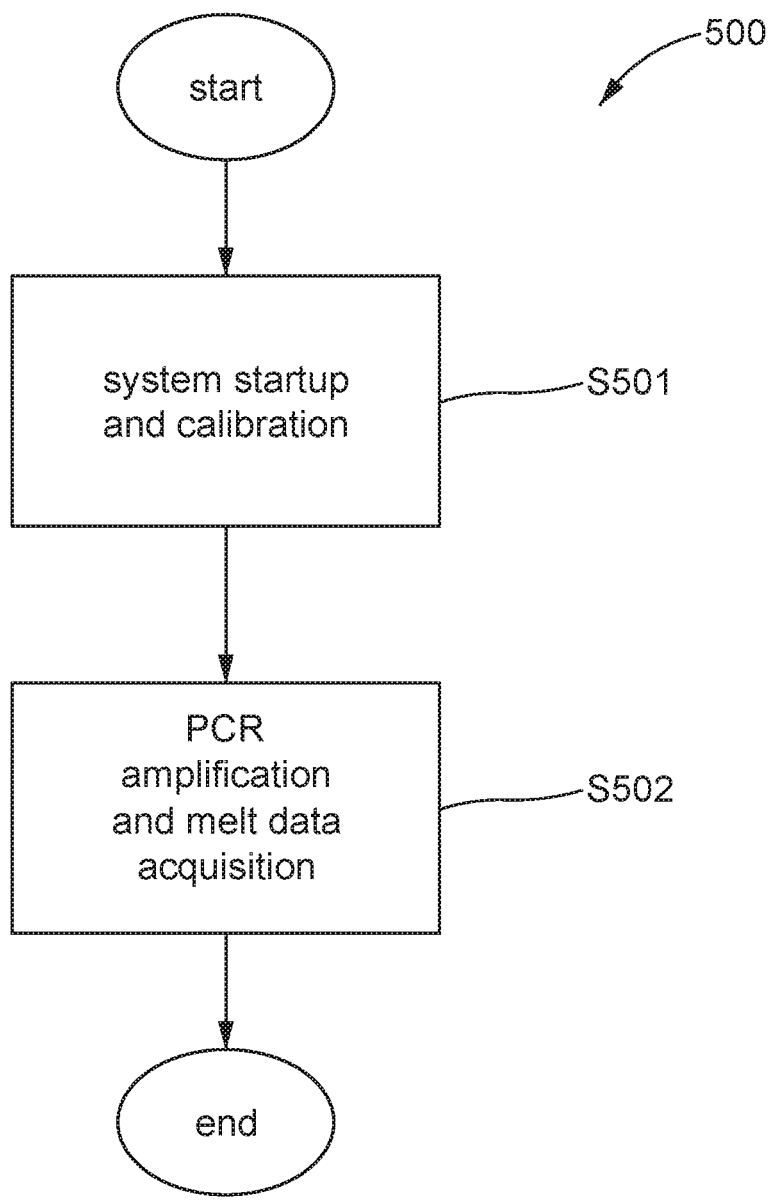
FIG. 5 illustrates a single slug process for performing system startup, calibration, PCR amplification, and melt data acquisition according to aspects of the present invention.

FIG. 5 illustrates a single slug process 500 for performing PCR amplification and melt data acquisition in a microfluidic reaction system (e.g., microfluidic reaction system 300) according to an embodiment of the present invention. The process 500 may include a step S501 at which the microfluidic reaction system performs system startup and calibration. The process 500 may also include a step S502 at which the microfluidic reaction system performs PCR amplification and melt data acquisition. The process 500 will be described in further detail below, with additional reference to FIGS. 6, 7, and 8A through 8L.

Figure 6:
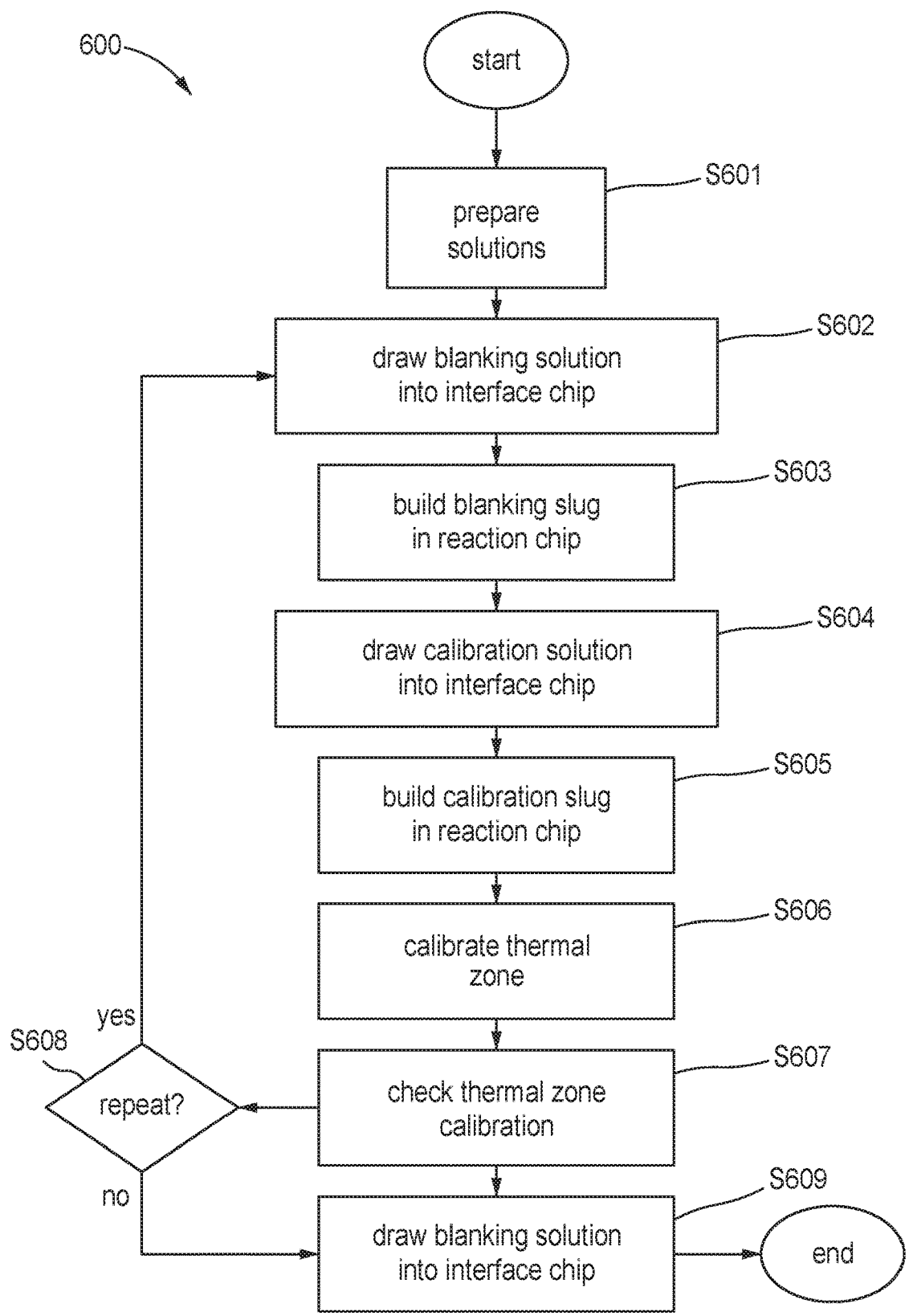
FIG. 6 illustrates a single slug process for performing system startup and calibration according to aspects of the present invention.
Figure 7:
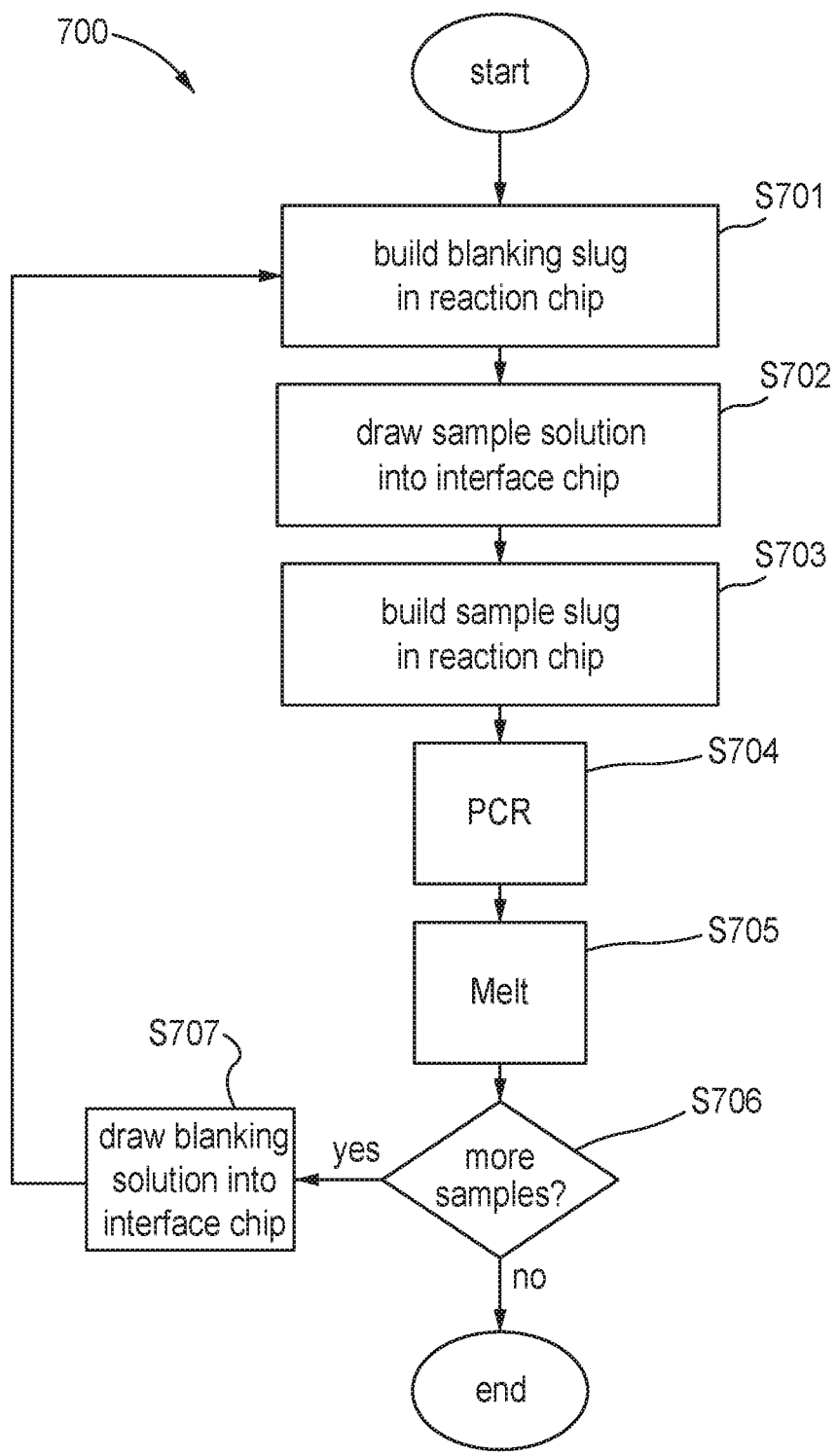
FIG. 7 illustrates a single slug process for performing PCR amplification and melt data acquisition according to aspects of the present invention.

FIG. 6 illustrates a single slug process 600 for performing the system startup and calibration of step S501 according to a non-limiting embodiment of the present invention, and FIG. 7 illustrates a single slug process 700 for performing the PCR amplification and melt data acquisition of step S502 according to a non-limiting embodiment of the present invention. FIGS. 8A through 8L illustrate the steps of the processes 500, 600, and 700 in relation to the embodiment of the interface chip 102 and the reaction chip 104 of the microfluidic device 100 illustrated in FIGS. 1 and 2. An exemplary timing diagram for process 600 is illustrated in FIG. 9A, and an exemplary timing diagram for process 700 is illustrated in FIG. 9B.

In some embodiments, the single slug process 600 for performing the system startup and calibration of step S501 may establish a slug edge for closed loop flow control and may calibrate the one or more heating elements 220 of the thermal zone 218. As a result, the system timing in process 600 may be slightly different for the first set of slugs compared to system timing in the process 700 for performing the PCR amplification and melt data acquisition of step S502. Running the first set of slugs and performing calibration may be referred to as the startup cycle. The process 600 may be executed by the microfluidic reaction system 300 under the control of system controller 348.

In some embodiments, when the startup process 600 begins, the preparation stage 338, which may include PCR and blanking robots, may not have fluids loaded in their pipettes. As illustrated in FIG. 6, the single slug system startup and calibration process 600 may include a step S601 in which the system controller 348 commands the preparation stage 338 to prepare blanking solution 344 and calibration solution 346 for delivery to the microfluidic device 100. For example, in some non-limiting embodiments, the preparation stage 338 may receive a "Build Test (Cal fluid)" command from the system controller 348, and, in response, a PCR robot of the preparation stage 338 may queue up steps for a PCR robot to clean one or more pipette tips and pick up one or more appropriate fluids (e.g., calibration solution 346). Further, in some non-limiting embodiments, the preparation stage 338 may receive "Build Blank" command from the system controller 348, and, in response, may move a blanking robot of the preparation stage 338 to blanking wells on a cartridge, where the blanking robot draws/aspirates blanking solution/fluid 344 into one or more pipette tips. The blanking robot may then move to sippers on a cartridge.

In some non-limiting embodiments, during step S601, the flow controller 350 may stop flow in the interface chip 102 (i.e., K-chip) and/or cause flow control in the reaction chip 104 to go into an idle mode with no edge control. In a non-limiting embodiment, the heating controller 352 may set the temperature of the thermal zone 218 (i.e., Zone 1) to a default temperature (e.g., the minimum temperature used in the calibration melt). In some non-limiting embodiments, the detection system 354 may turn on excitation devices 366, 372, or 376, which may include a red LED, to illuminate the blanking solution for tracking purposes.

A non-limiting example of the processing that may be performed in step S601 is illustrated in FIG. 9A with reference to the "Slug Startup" step.

In some embodiments, the single slug system startup and calibration process 600 may include a step S602 in which the flow controller 350 draws/aspirates the blanking solution 344 into the microfluidic channel 108 of the interface chip 102 (K-chip) via an inlet port 106. In some embodiments, the blanking solution 344 may be flushed through the microfluidic channel 108 of the interface chip 102 and the T-junction 477. In some non-limiting embodiments where the flow of blanking solution 344 is the first flow into the microfluidic device 100, open loop flow control may be used to draw the blanking solution 344 into the microfluidic channel 108 of the interface chip 102.

In some embodiments, the blanking solution 344 drawn into the interface chip 102 in step S602 may be received from a bead dispensed by the preparation stage 338. In some non-limiting embodiments, in step S602, the flow controller 350 may begin ramping in the interface chip 102 at a ramp rate ($nL/s^2$), which may be user defined. The flow controller 350 may ramp up flow in the interface chip 102 from 0 nL/s to a user defined flow rate. The flow controller 350 may then maintain a constant flow for a fixed period before ramping down at a ramp rate, which may be the same as the ramp up rate and may be user defined. The total time (as well as the constant flow time) may be determined by a user defined volume (time=volume/avg. flow rate).

During the aspiration of the blanking solution/fluid 344, the intensity level (e.g., red intensity level) may be measured at a T-junction 477 of each channel 108 (e.g., by detection device 368). The intensity level(s) may be measured at the K-flow ROIs 491 to determine the actual fill time for each channel. In a non-limiting embodiment, the flow controller 350 may stop flow in the interface chip 102 (i.e., K-flow) once the K-flow ROI increases above the K-flow threshold or an allotted time expires.

In some embodiments, after the flow controller 350 stops flow in the interface chip 102, the system controller 348 may command the preparation stage to build the next blank slug. In some embodiments, flow controller 350 may leave flow control in the reaction chip 102 (U-chip) in an "Idle" mode, which may allow blanking solution 344 to flow naturally into the reaction chip 102 through the T-junction 477 so that the blanking solution 344 remains intact as a slug and can be controlled in step S603 (described below). Thus, this type aspiration may be considered open-loop flow aspiration.

Figure 8A:
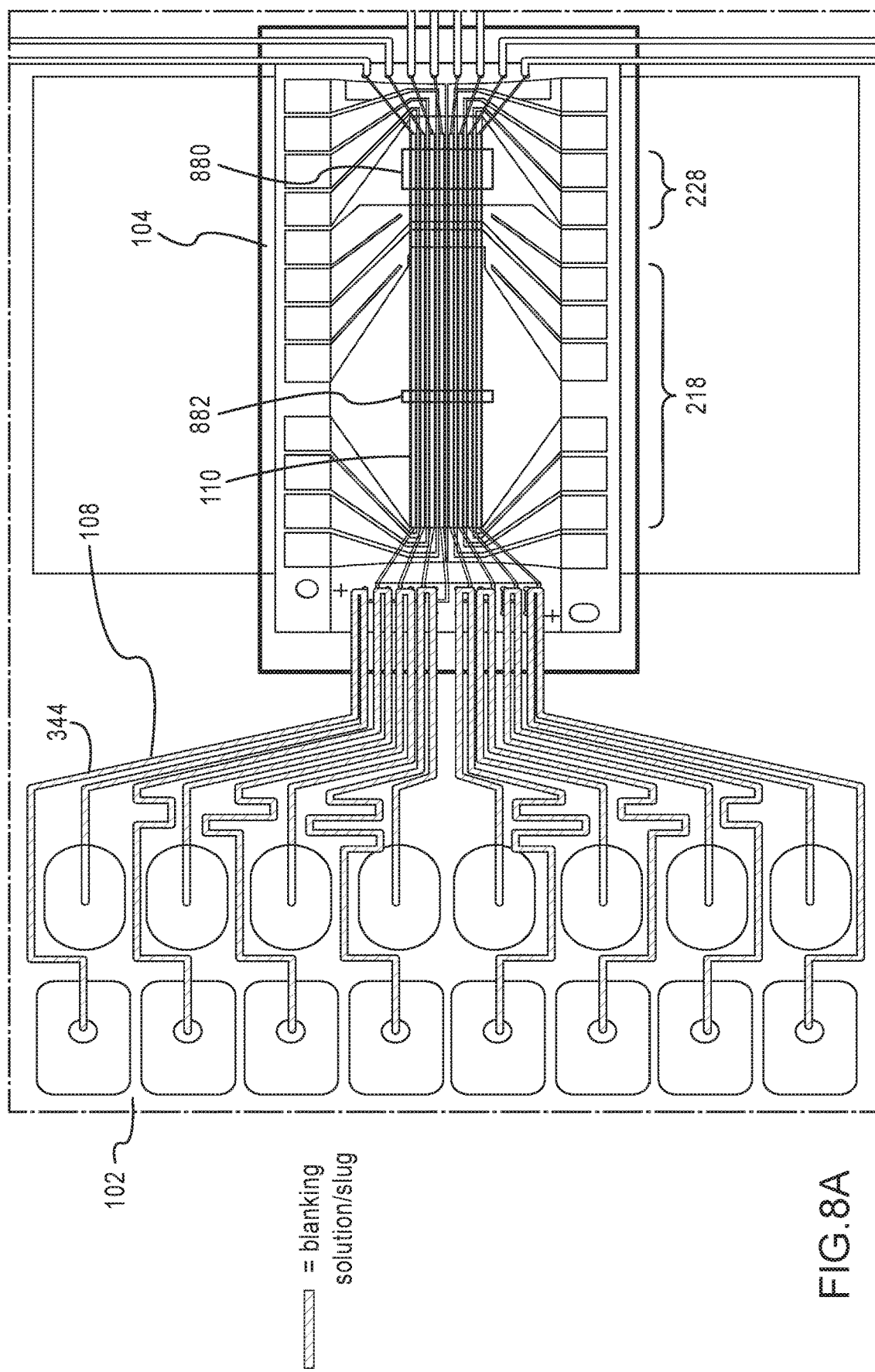
FIGS. 8A through 8L illustrate solutions/slugs moving through a microfluidic device according to a single slug approach according to aspects of the present invention.
Figure 9A:
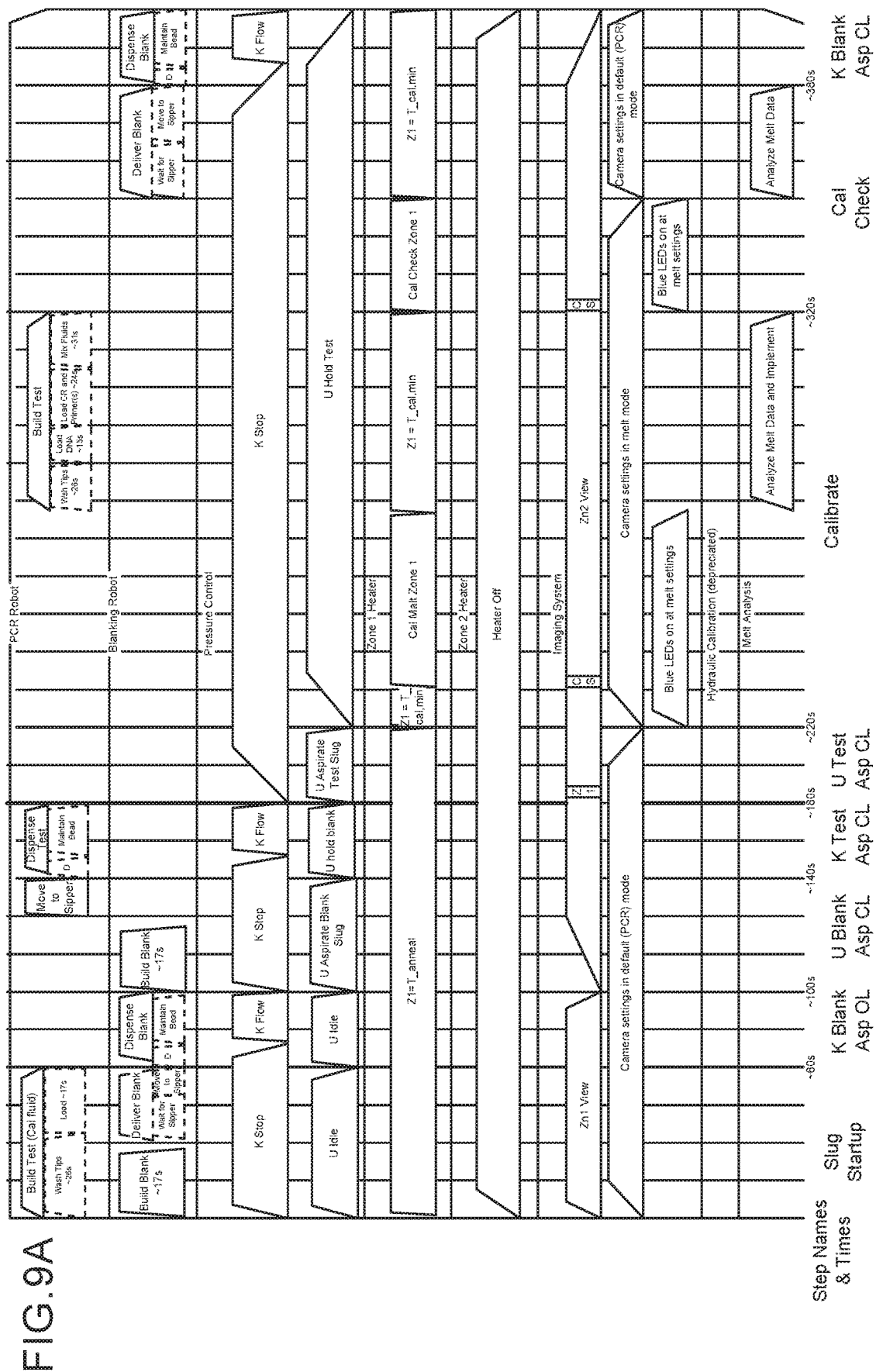
FIGS. 9A and 9B illustrate a timing diagram for performing system startup, calibration, PCR amplification, and melt data acquisition according to aspects of the present invention.
Figure 9B:
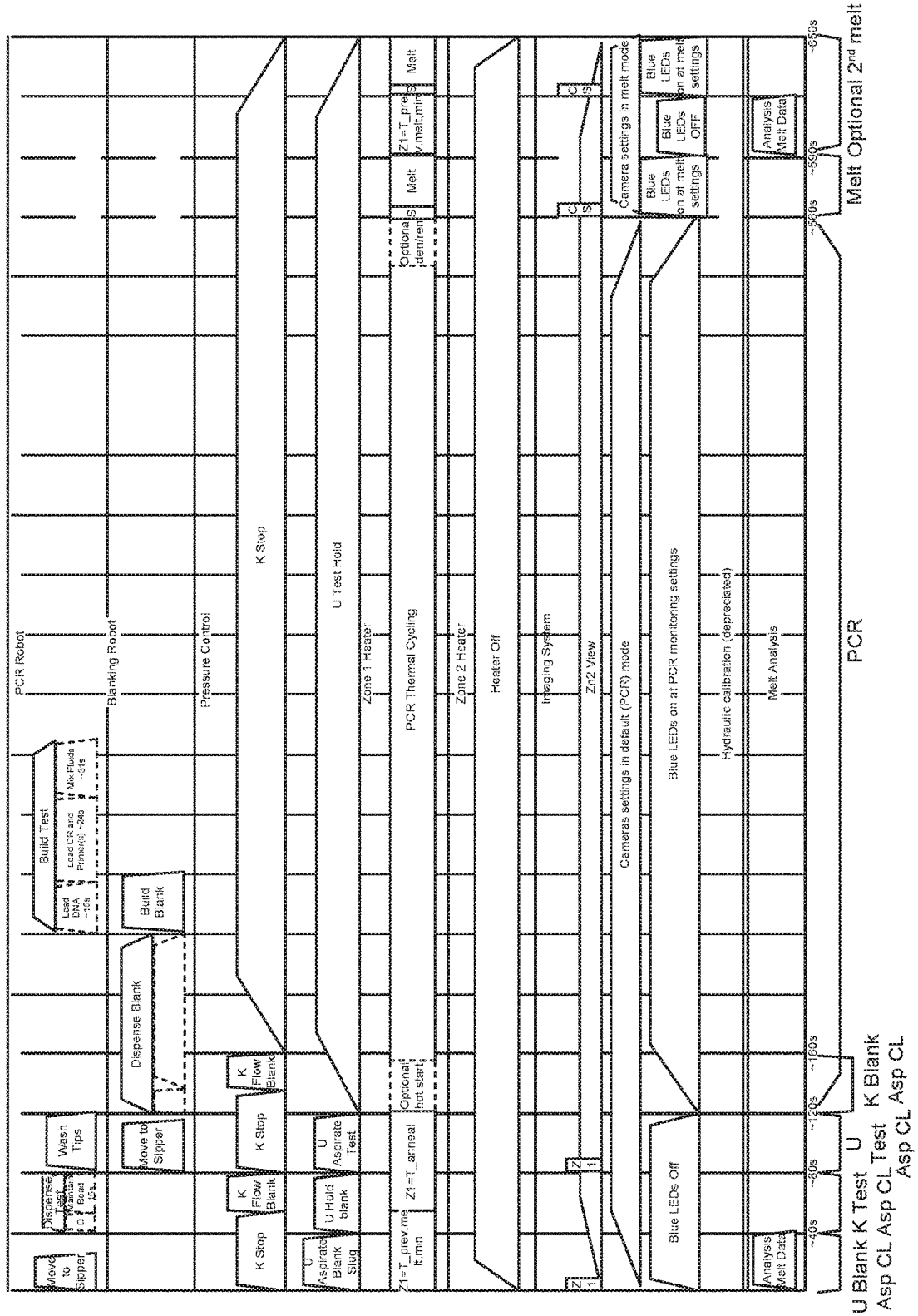

FIG. 8A illustrates an example of the blanking solution 344 drawn into the one or more channels 108 of the interface chip 102 during the step S602. A detailed example of the processing that may be performed in step S602 is illustrated in FIG. 9A with reference to the "K Blank Asp OL" step.

In some embodiments, the single slug system startup and calibration process 600 may include a step S603 in which the flow controller 350 builds a blanking slug 878 by drawing/aspirating the blanking solution 344 into the microfluidic channel 110 of the reaction chip 104 (U-chip). In some embodiments, the flow controller 350 may draw the blanking solution 344 into the microfluidic channel 110 of the reaction chip 104 until the leading edge of the blanking slug 878 reaches a slug building target region 880.

In some embodiments, during the step S603, the flow controller 350 may stop flow in the interface chip 102. In some embodiments, while the blanking solution 344 is being drawn into the reaction chip 104, the detection system 354 may monitor the leading edge of the blanking slug 878 and compare the actual location of the leading edge of the blanking slug 878 to a target blank location, which may be in the slug building target region 880. The flow controller 350 may use feedback from the detection system 354 (e.g., PID control) to determine a desired flow rate in the reaction chip 104. Also, during step S603, system controller 348 may control a blanking robot of the preparation stage 338 to move to the blanking wells and build another blanking slug in pipette tips. In a non-limiting embodiment, once the blanking robot has built the blanking slug, system controller 348 may control a PCR robot to move to the sipper to prepare to dispense calibration solution 346 in step S604.

Figure 8B:
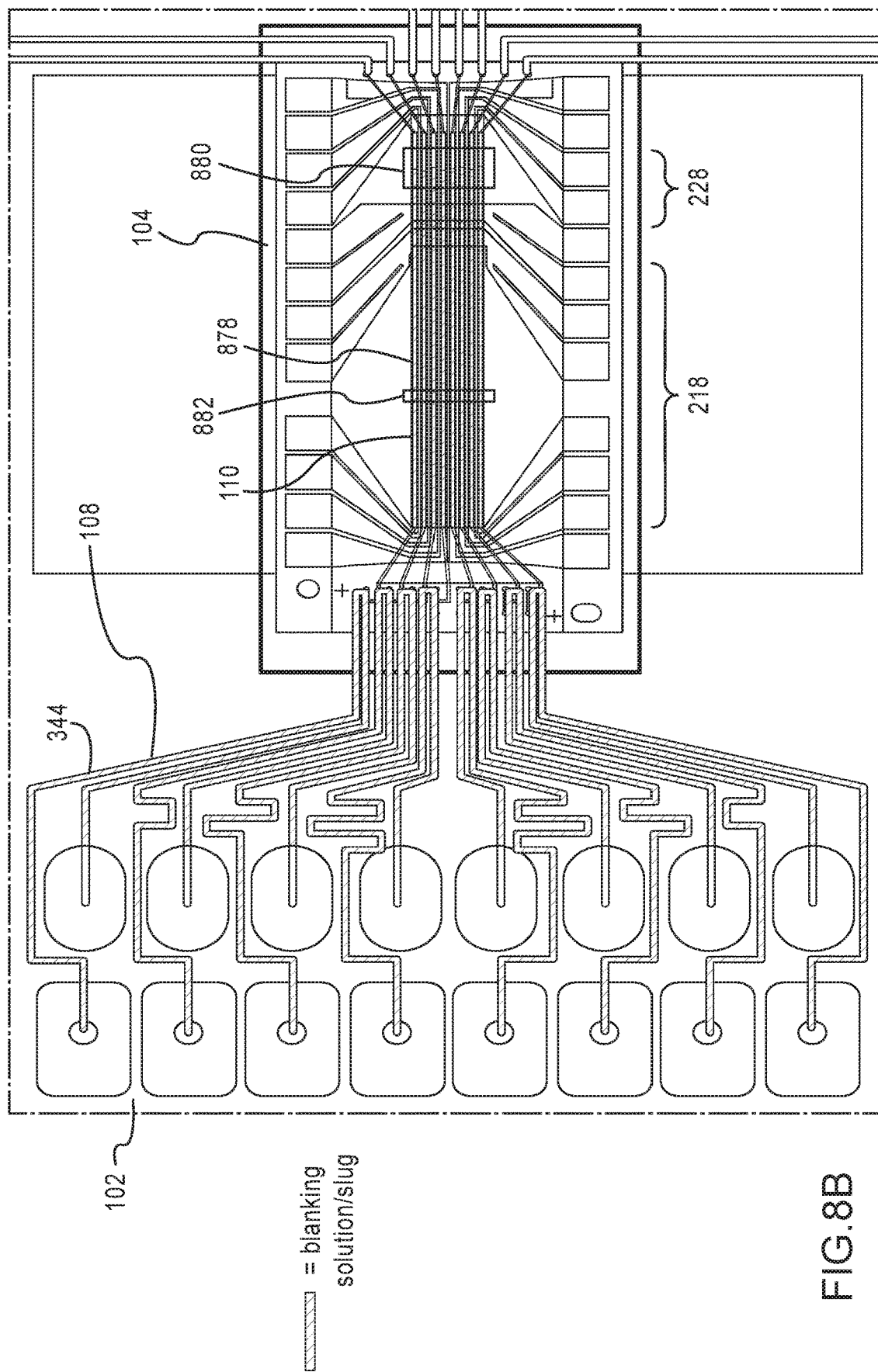

FIG. 8B illustrates an example of the blanking slug 878 built in the one or more channels 110 of the reaction chip 104 during the step S603. A detailed example of the processing that may be performed in step S603 is illustrated in FIG. 9A with reference to the "U Blank Asp CL" step.

In some embodiments, the single slug system startup and calibration process 600 may include a step S604 in which the flow controller 350 draws/aspirates the calibration solution 346 into the interface chip 102. In step S604, the system controller 348 may command the PCR robot in the preparation stage 338 to dispense a bead of calibration solution 346. During step S604, the flow controller 350 may hold the blanking slug 878 in the reaction chip 104. In a non-limiting embodiment, the flow controller 350 may use a different set of PID constants to maintain the leading edge of the blanking slug 878 in position in the slug building target region 880. The flow controller 350 may draw the calibration solution 346 into the interface chip 102 according to a ramp profile, which, in some embodiments, may have a user definable volume, ramp rate, and flow rate.

Figure 8C:
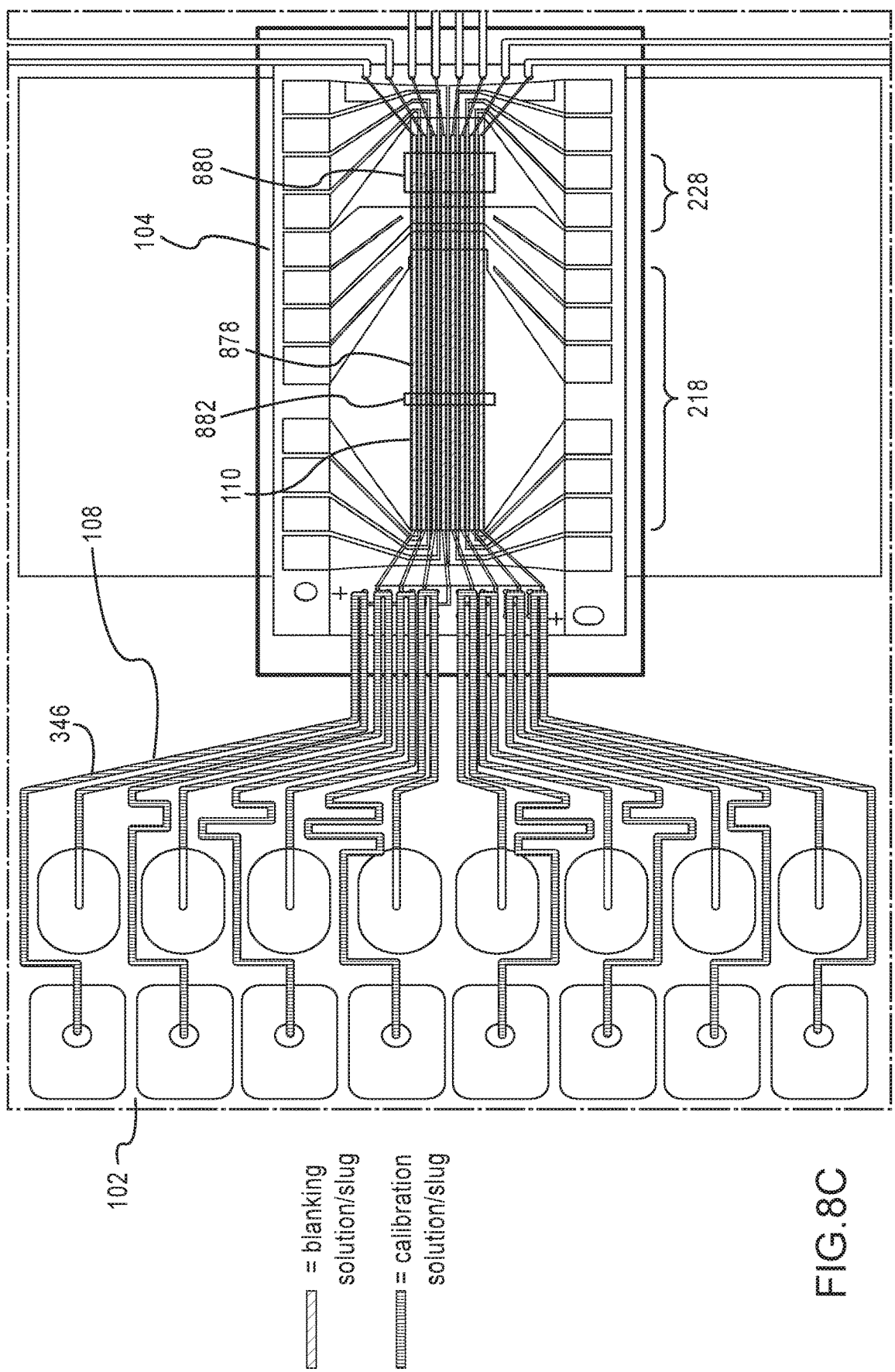

FIG. 8C illustrates an example of the calibration solution 346 drawn into the one or more channels 108 of the interface chip 102 during the step S604. A detailed example of the processing that may be performed in step S604 is illustrated in FIG. 9A with reference to the "K Test Asp CL" step.

In some embodiments, the single slug system startup and calibration process 600 may include a step S605 in which the flow controller 350 builds a calibration slug 884 (see FIGS. 8D and 8E) by drawing/aspirating the calibration solution 346 into the microfluidic channel 110 of the reaction chip 104 (U-chip). In some embodiments, the flow controller 350 may draw the calibration solution 346 into the microfluidic channel 110 of the reaction chip 104 until the trailing edge of the blanking slug 878 reaches a slug building target region 880. In some embodiments, the flow controller 350 may use feedback from detection system 354 for control and to maintain the trailing edge of the blanking slug 878 at a target position within the slug building target region 880, which may be in the second zone 228. In some embodiments, the detection system 354 may monitor the trailing edge of the blanking slug 878 at a reaction chip flow control/slug control ROI 1096 (i.e., U-flow ROI).

Figure 8D:
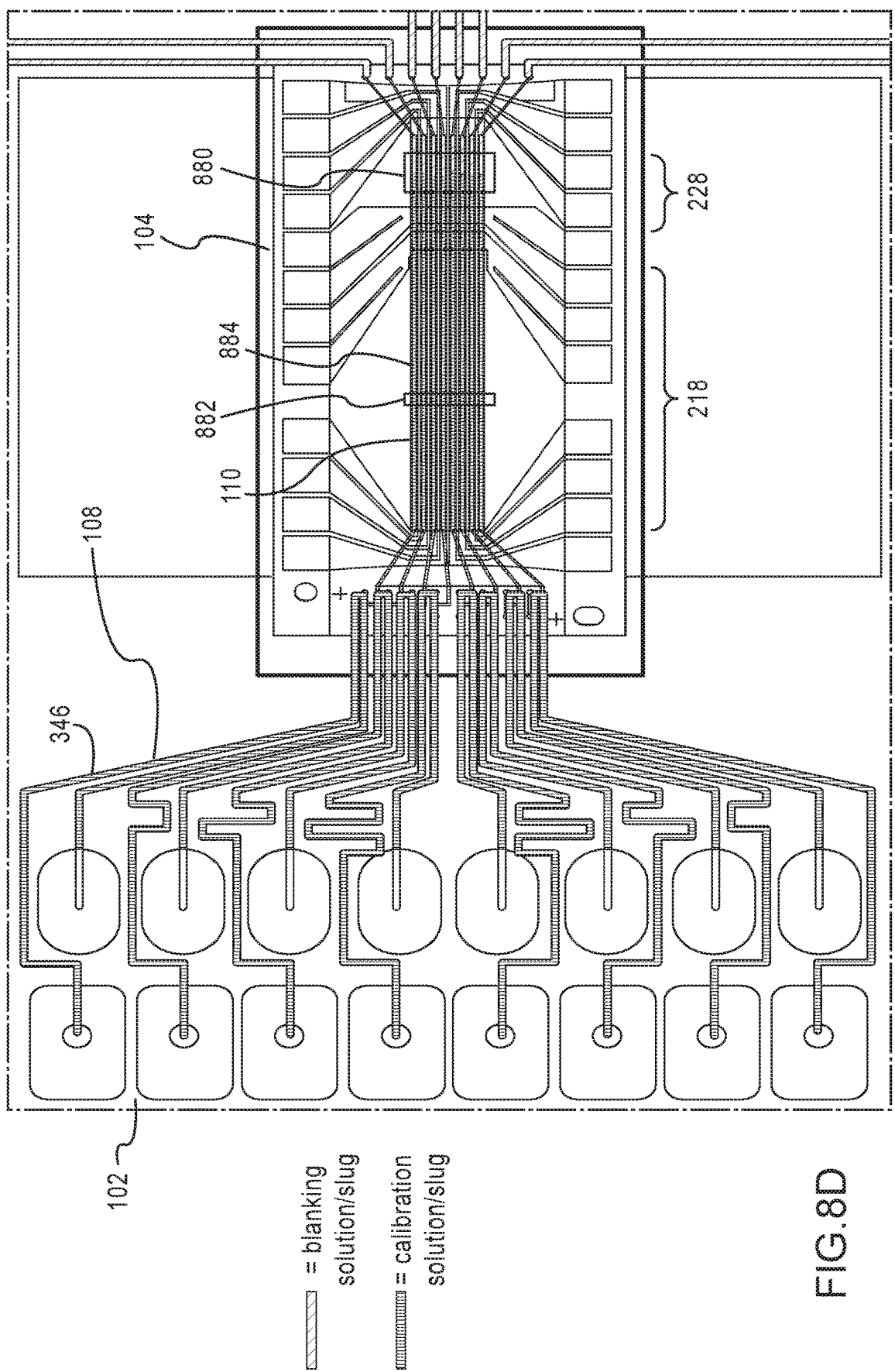

FIG. 8D illustrates an example of the calibration slug 884 built in the one or more channels 110 of the reaction chip 104 during the step S605. A detailed example of the processing that may be performed in step S605 is illustrated in FIG. 9A with reference to the "U Test Asp CL" step.

In some embodiments, the single slug system startup and calibration process 600 may include a step S606 in which the heating controller 352 may control a heating element 220 to heat the portion of the calibration slug 884 in the thermal zone 218 of the reaction chip 104 according to the temperature ramp profile. In some embodiments, during heating of the portion of the calibration slug 884 in the thermal zone 218 according to the temperature ramp profile, the detection system 354 may control the thermal zone excitation device 374 and thermal zone detection device 376 to measure fluorescence from the portion of the calibration slug 884 in the thermal zone 218. In some embodiments, the melt analyzer 356 may perform a calibration melt analysis to determine calibration coefficients based on the measured fluorescence.

In some embodiments, the calibration coefficient may be determined for each heating element 220, which may also act as a temperature sensor. The temperature ramp profile may include, for example, starting and ending temperatures (i.e., a melt range) and the temperature ramp rate. In some embodiments, the parameters of the temperature ramp profile may be user definable.

In a non-limiting embodiment, the heating controller 352 may set the thermal zone 218 (Zone 1) heater temperatures to the minimum temperature used in the melt. The detection system 354 may turn on thermal zone excitation device 374 (e.g., one or more blue LEDs) to its melt (high power) settings, which may be user definable. The thermal zone detection device 376 may measure fluorescence from the thermal zone 218 (e.g., from PCR/melt ROIs 1098) during the melt.

In a non-limiting embodiment, the detection system 354 may control the thermal zone detection device 376, which may include a camera, to take a snapshot of the reaction chip 104, and, the detection system 354 may receive a time stamped full frame image in return. The time stamp and the time at which the detection system 354 issues the take snapshot command may be used to synchronize the detection system 354 with internal camera controllers. In one embodiment, the heating controller 352 may then begin the thermal ramp of the heating elements 220 for thermal zone 218 (Zone 1). The heating elements 220 may be controlled by PID parameters, which may be user definable. During the melt data acquisition, images may be stored in a buffer.

In some embodiments, once the melt data acquisition completes, the heating elements 220 may be returned to the minimum temperature of the temperature ramp, and/or the analysis of the melt data may begin. In a non-limiting embodiment, images taken during the melt may be read from the buffer, and the fluorescence measured by the thermal zone detection device 376 from the thermal zone 218 (e.g., from PCR/melt ROIs 1098) during the melt may be used to determine fluorescence intensities for each channel 110.

In one non-limiting embodiment, a calibration reference file, which may be user defined, may then be used as an input, along with the fluorescence intensities and data from the heating element/sensor 220, in a dual point calibration routine such as, for example, a peak picker. The peak picker may return a new set of calibration coefficients (e.g., k0's and k1's) for each of the 8 heaters in the thermal zone 218 (Zone 1) based on the known melting temperature of the calibration solution. In an embodiment, the peak picker may present a dialog to the user to determine their acceptability. In some non-limiting embodiments, the system 300 may determine the calibration coefficients in the manner described in U.S. Patent Application Publication No. 2012/0051390, which is incorporated by reference herein in its entirety.

Also, in some embodiments, during step S606 (e.g., once the thermal melt and concurrent analysis is complete), the system controller 348 may control a PCR robot of the preparation stage 338 to build of the first sample slug (i.e., first assay or test slug). In a non-limiting embodiment, the PCR robot of the preparation stage 338 may build the first sample slug by, for example, cleaning the pipette tips at wash rollers, picking up three solutions/fluids (e.g., sample/DNA 340, common reagent 342, and primer master mix) in defined volumes, and mixing the solutions.

At the end of step S606, one or more calibration slugs 884 may still be held in the microfluidic channels 110 of the reaction chip 104 as shown in FIG. 8D. A detailed example of the processing that may be performed in step S606 is illustrated in FIG. 9A with reference to the "Calibrate" step.

In some embodiments, the single slug system startup and calibration process 600 may include a step S607 in which the single slug system 300 performs a check of the thermal calibration. The check may involve a melt analysis of the same calibration solution slug 884 already in the microfluidic channel 110 of the reaction chip 104 using the calibration coefficients (e.g., heating element coefficients) determined in step S606.

In step S607, the detection system 354 may turn on thermal zone excitation device 374 (e.g., one or more blue LEDs) to its melt (high power) settings. The detection system 354 may perform a camera sync operation. The heating controller 352 may control a heating element 220 to heat the portion of the calibration slug 884 in the thermal zone 218 of the reaction chip 104 according to the temperature ramp profile, which may be user defined. During melt, the thermal zone detection device 376 may measure fluorescence from the thermal zone 218 and may take images, which may be high speed images, and store the images in a melt buffer.

After the completion of the thermal ramp, the heating controller 352 may return the heating elements 220 associated with the thermal zone 218 (Zone 1) to the minimum temperature used in the ramp, the detection system 354 may return the camera to default (PCR) mode, and the melt analyzer 356 may begin analysis of the acquired melt data. In a non-limiting embodiment, after the completion of the thermal ramp (e.g., concurrently with the melt analysis), the system controller 348 may control the blanking robot to the sippers to prepare for the next delivery of one or more beads of blanking solution.

In some non-limiting embodiments, the single slug system startup and calibration process 600 may include a step S608 in which, once the melt analysis is completed, the system 300 may pause for a user to review the results of the calibration check (i.e., the check melt results). At this point, the calibration can be accepted (continue), the check melt can be redone (remelt), a new calibration slug can be created to retry the entire calibration process (retry new calibration slug/repeat), or the panel can be abandoned (reset). If the calibration is accepted, the process 600 may proceed to step S609. If the user requests that the calibration be repeated, the process 600 repeats the calibration process (e.g., by proceeding back to step S602 to repeat steps S602-S608).

At the end of steps S607 and S608, calibration solution 346 may still be held in the microfluidic channels 108 of the interface chip 102, and calibration slugs 884 may still be held in the microfluidic channels 110 of the reaction chip 104, as shown in FIG. 8D. A detailed example of the processing that may be performed in step S607 is illustrated in FIG. 9A with reference to the "CalCheck" step.

In some non-limiting embodiments, the single slug system startup and calibration process 600 may include a step S609 in which the flow controller 350 draws/aspirates the blanking solution 344 into the interface chip 102. In step S609, the system controller 348 may command the blanking robot in the preparation stage 338 to dispense a bead of blanking solution 344. During step S609, the flow controller 350 may hold the calibration slug 884 in the reaction chip 104. In a non-limiting embodiment, the flow controller 350 may use a set of PID constants to maintain the trailing edge of the blanking slug 878 in position in the slug building target region 880. The flow controller 350 may draw the sample solution 340 into the interface chip 102 according to a ramp profile, which, in some embodiments, may have a user definable volume, ramp rate, and flow rate.

Figure 8E:
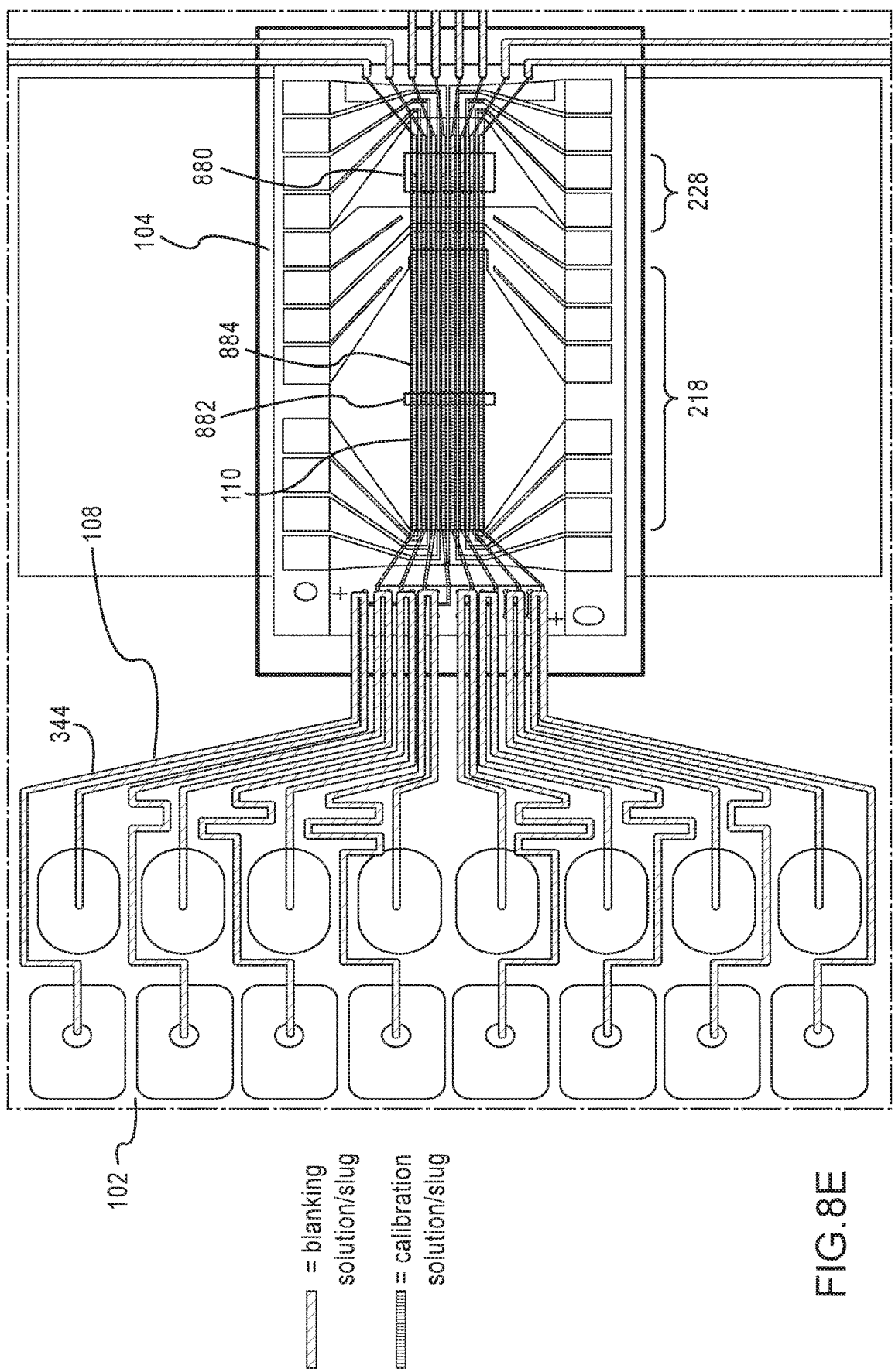

FIG. 8E illustrates an example of the blanking solution 344 drawn into the one or more channels 108 of the interface chip 102 and the calibration slug 884 held in the microfluidic channels 110 of the reaction chip 104 during the step S609. A detailed example of the processing that may be performed in step S609 is illustrated in FIG. 9A with reference to the "K Blank Asp CL" step.

In some embodiments, the single slug process 700 for performing the PCR amplification and melt data acquisition may include a step S701 in which the flow controller 350 builds a blanking slug 878 by drawing/aspirating the blanking solution 344 from a microfluidic channel 108 of the interface chip 102 into the microfluidic channel 110 of the reaction chip 104 (U-chip). In some embodiments, the flow controller 350 may draw the blanking solution 344 into the microfluidic channel 110 of the reaction chip 104 until the leading edge of the blanking slug 878 reaches a slug building target region 880.

In some embodiments, during the step S701, the flow controller 350 may stop flow in the interface chip 102. In some embodiments, while the blanking solution 344 is being drawn into the reaction chip 104, the detection system 354 may monitor the leading edge of the blanking slug 878 and compare the actual location of the leading edge of the blanking slug 878 to a target blank location, which may be in the slug building target region 880. The flow controller 350 may use feedback from the detection system 354 (e.g., PID control) to determine a desired flow rate in the reaction chip 104 to correct the actual edge location to the target edge location. Also, during step S701, the system controller 348 may control a PCR robot to move to the sipper to prepare for a sample solution dispense in step S702.

In some embodiments, during the step S701, the heating controller 352 maintains the heating elements 220 in the thermal zone 218 (Zone 1) at the minimum temperature from a prior melt (e.g., in step S607 in cycle 1 of process 600 or in step S705 in cycles 2-N of process 700). The detection system 354 may keep the thermal zone excitation device 374 (e.g., one or more blue LEDs) off.

In some embodiments, during step S701, the detection system 354 may control the interface detection device 368 to check that the blanking solution has filled the T-junction 477. In one embodiment, the one or more flow control regions of interest (ROIs) 491 (e.g., K-flow ROI(s)) may be used for this check. In embodiments where the detection system 354 must switch between views, the detection system 354 may briefly (e.g., 3s) switch to the K-flow ROIs 491 before switching back to the U-flow ROIs 1096 so that blanking slug control in the slug building target region 880 may be maintained.

At the end of step S701, the flow controller 350 may determine the proper aspiration of blanking solution in the reaction chip 104 by using feedback from the detection system 354. For example, the detection system 354 may use signals detected from regions of interest 1096 in the second zone of the reaction chip 104 (i.e., U-flow ROIs 1096). In one embodiment, the flow controller 350 may use the feedback from the U-flow ROIs 1096 to verify that the solutions in the U-flow ROIs 1096 have a particular color, such as bright red (e.g., to verify that the red signal has increased above the threshold), and, thus, have been filled with blanking solution. If any of the channels fail to fill, the system controller 348 may present a retry/reset warning dialog to the user (if the option for warning dialogs is checked).

Figure 8F:
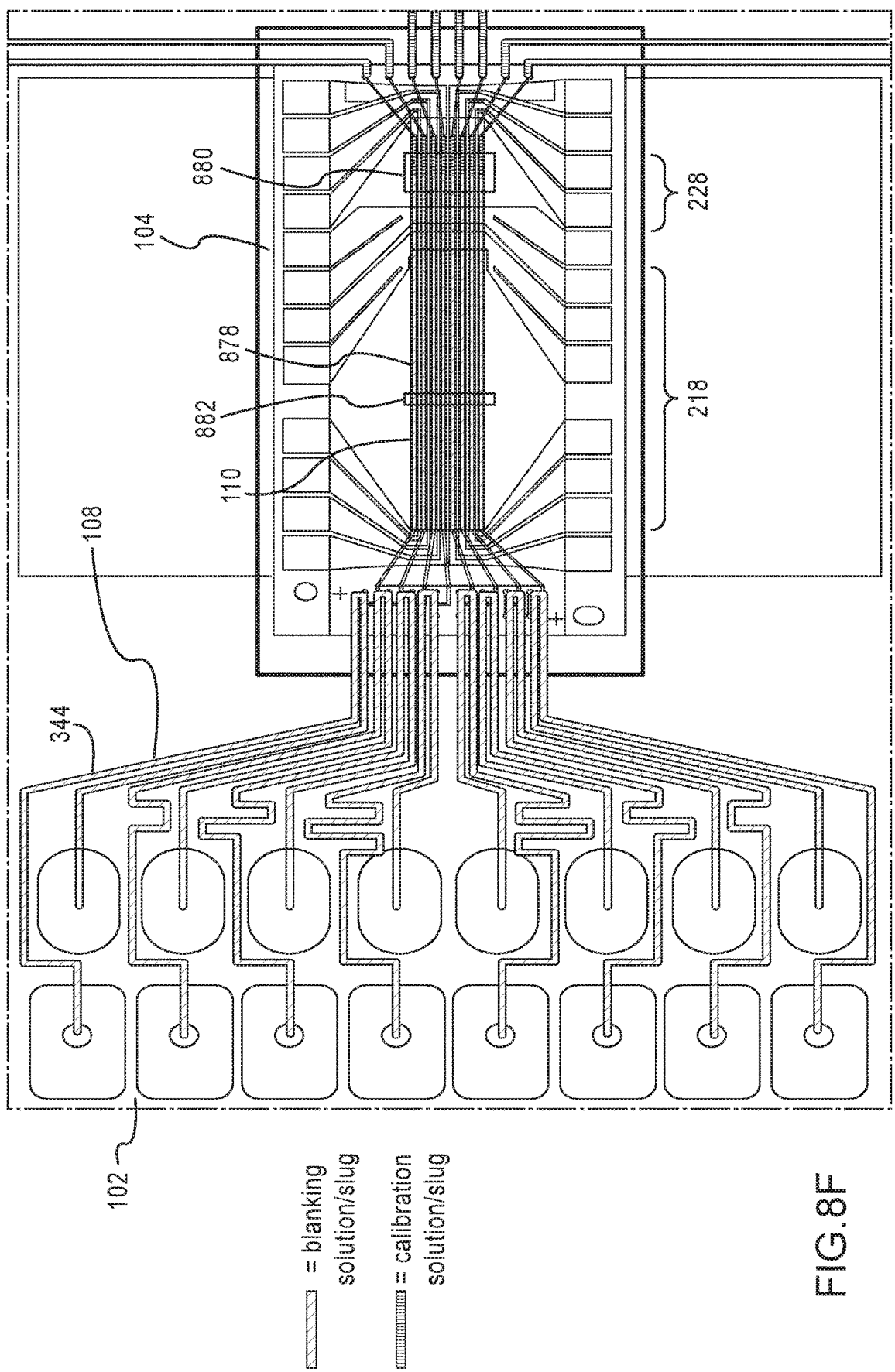

FIG. 8F illustrates an example of the blanking slug 878 built in the one or more channels 110 of the reaction chip 104 during the step S701 with a leading edge in the slug building target region 880. A detailed example of the processing that may be performed in step S701 is illustrated in FIG. 9B with reference to the "U Blank Asp CL" step.

Figure 8G:
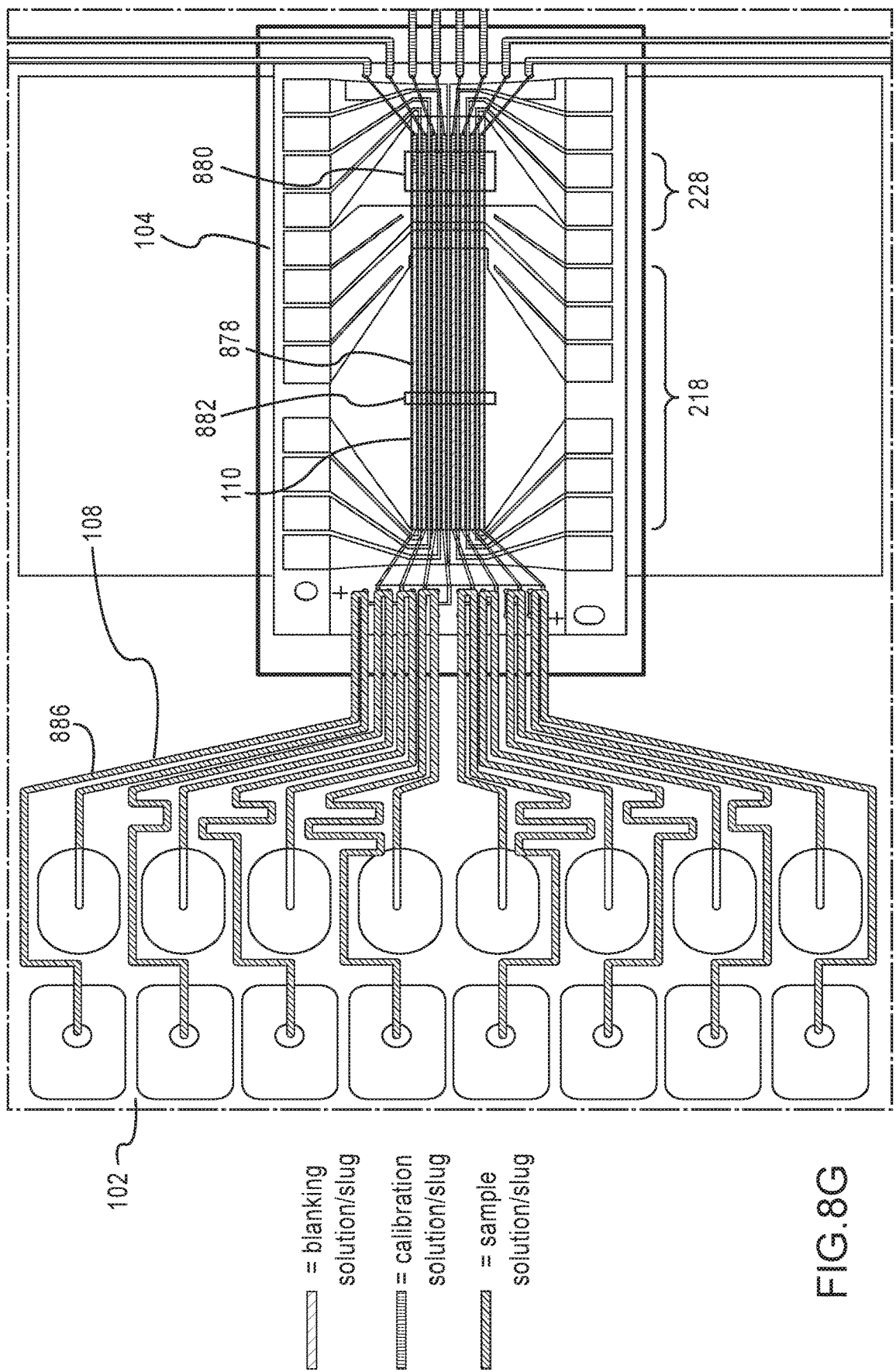

In some embodiments, the single slug process 700 for performing the PCR amplification and melt data acquisition may include a step S702 in which the flow controller 350 draws/aspirates the sample solution 886 into the interface chip 102 (see FIG. 8G). In step S702, the system controller 348 may command the PCR robot in the preparation stage 338 to dispense a bead of sample solution 886. In a non-limiting embodiment, the heater elements 220 may set temperatures in the thermal zone 210 (Zone 1) to the annealing temperature, which may be the minimum temperature in the PCR profile.

During step S702, the flow controller 350 may hold the blanking slug 878 in the reaction chip 104. In a non-limiting embodiment, the flow controller 350 may use a set of PID constants to maintain the leading edge of the blanking slug 878 in position in the slug building target region 880. The flow controller 350 may draw the sample solution 886 into the interface chip 102 according to a ramp profile, which, in some embodiments, may have a user definable volume, ramp rate, and flow rate.

In some non-limiting embodiments, during step S702, the heating controller 352 sets the thermal zone 218 (Zone 1) temperatures to the annealing temperature, which is usually the minimum temperature in the PCR profile.

FIG. 8G illustrates an example of the sample solution 886 drawn into the one or more channels 108 of the interface chip 102 during the step S702. A detailed example of the processing that may be performed in step S702 is illustrated in FIG. 9B with reference to the "K Test Asp CL" step.

In some embodiments, the single slug process 700 for performing the PCR amplification and melt data acquisition may include a step S703 in which the flow controller 350 builds a sample slug 888 (see FIG. 8H) by drawing/aspirating the sample solution 886 into the microfluidic channel 110 of the reaction chip 104 (U-chip). In some embodiments, the flow controller 350 may draw the sample solution 886 into the microfluidic channel 110 of the reaction chip 104 until the trailing edge of the blanking slug 878 reaches a slug building target region 880. In some embodiments, the flow controller 350 may use feedback from detection system 354 for control and to maintain the trailing edge of the blanking slug 878 at a target position within the slug building target region 880, which may be in the second zone 228. In some embodiments, the detection system 354 may monitor the trailing edge of the blanking slug 878 at a reaction chip flow control/slug control ROI 1096 (i.e., U-flow ROI).

In some embodiments, during step S703, the flow controller 350 may stop flow in the interface chip 102. In some non-limiting embodiments, during step S703, system controller 348 may control the PCR robot of the preparation stage 338 to clean pipette tips at the cleaning station and control the blanking robot to move to the sippers.

In some embodiments, during step S703, the detection system 354 may control the interface detection device 368 to check that the sample solution 886 has filled the T-junction 477. In one embodiment, the one or more flow control regions of interest (ROIs) 491 (e.g., K-flow ROI(s)) may be used for this check. In embodiments where the detection system 354 must switch between views, the detection system 354 may briefly (e.g., 3s) switch to the K-flow ROIs 491 before switching back to the U-flow ROIs 1096 so that blanking slug control in the slug building target region 880 may be maintained.

At the end of step S703, the flow controller 350 may determine the proper aspiration of sample solution in the reaction chip 104 by using feedback from the detection system 354. For example, the detection system 354 may use signals detected from regions of interest 1096 in the second zone of the reaction chip 104 (i.e., U-flow ROIs 1096). In one embodiment, the flow controller 350 may use the feedback from the U-flow ROIs 1096 to verify that the U-flow ROIs 1096 have turned dark (e.g., verify that the signal has decreased from a particular color (red) below a threshold), and, thus, have filled with sample solution. If any of the channels fail to fill, the system controller 348 may present a retry/reset warning dialog to the user (if the option for warning dialogs is checked).

At the end of step S703, the proper aspiration of sample solution in the reaction chip 104 (U-chip) may be determined by evaluating flow in the reaction chip 104 (i.e., by performing a Uflow check). In one embodiment, evaluating flow in the reaction chip 104 may use the Ucheck ROIs to verify that they have gone dark (red signal has decreased below the threshold). If any of the channels failed to fill, the retry/reset warning dialog may be presented to the user (if the option for warning dialogs is checked).

Figure 8H:
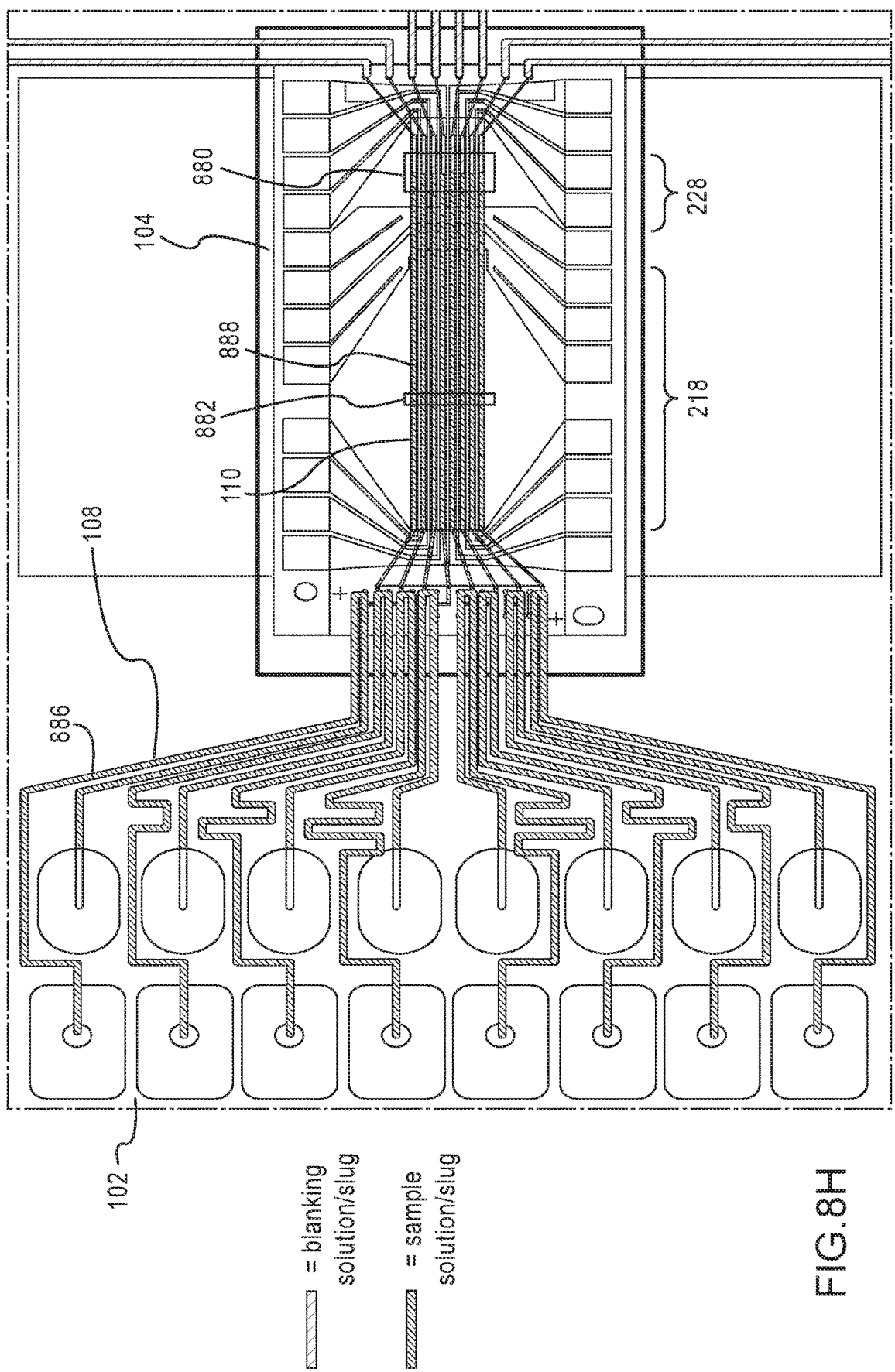

FIG. 8H illustrates an example of the sample slug 888 built in the one or more channels 110 of the reaction chip 104 during the step S703. A detailed example of the processing that may be performed in step S703 is illustrated in FIG. 9B with reference to the "U Test Asp CL" step.

In some embodiments, the single slug process 700 for performing the PCR amplification and melt data acquisition may include a step S704 in which the heating controller 352 controls the one or more heating elements 220 to heat a portion of the sample slug 888 in a thermal zone 218 of the reaction chip 104 to cycle the temperature of the portion of the sample slug 104 in the thermal zone according to a PCR amplification profile. In some embodiments, the PCR amplification profile may include denaturation total time and ramp time, annealing total time and ramp time, extension total time and ramp time, and a number of PCR cycles, which may be user defined. In some embodiments, the detection system 354 may control the thermal zone excitation device 374 and thermal zone detection device 376 to measure fluorescence from the thermal zone 218 (e.g., from the PCR/melt ROIs 1098) during PCR temperature cycling, and the heating controller 352 may control heating in the thermal zone 218 in accordance with real-time PCR in which one or more parameters of the temperature ramp profile is adjusted based on the measured fluorescence.

In some embodiments, if a user has selected to include the optional hot start (e.g., with user defined temperature and duration), then the hot start will precede thermal cycling according to the PCR amplification profile.

In step S704, the detection system 354 may set thermal zone excitation device 374 (e.g., one or more blue LEDs) to its PCR (low power) settings. Following a hot start (if selected), PCR thermal cycling in the thermal zone 218 (Zone 1) begins. The cycling parameters (denaturation total time and ramp time, annealing total time and ramp time, extension total time and ramp time, number of PCR cycles) may be user definable and may be stored in a database of system 300.

During step S704, the system controller 348 may control the PCR robot of the preparation stage 338 to prepare for the next test (e.g., by loading DNA samples 340 from DNA wells, then primer from the well array, and then common reagent 342 from the well array, where the volumes and well plate locations may be defined in a panel maker database, and then mixing the fluids).

During step S704, the detection system 354 may track the trailing edge of the blanking slug 878 (e.g., via the U-flow ROIs 1096), and the flow controller 350 may control the position of the sample slug 888 based on feedback from the detection system 354 to hold the trailing edge of the preceding blanking slug at a target location with the slug building target region 880.

In some embodiments, after the PCR cycles complete, the heating controller 352 may control the heating elements 220 to perform an optional denature/renature cycle in the thermal zone 218. The settings for denature/renature may be user definable. For instance, in one non-limiting embodiment, the settings for temperatures, dwell times, ramp times, and/or number of cycles of the denature/renature cycle may be user definable. In some embodiments, the denature/renature cycle may comprise a high temperature denaturation of the PCR product followed by a low temperature annealing of the product (a.k.a renaturation).

In some embodiments, in step S704, the system controller 348 may control the blanking robot of the preparation stage 338 to dispense blanking solution 344 and maintain the bead above the sippers. Once the bead is in place, the flow controller 350 may pull blanking solution 344 into the interface chip 102. The volume, flow rate, and ramp used by the flow controller 350 to pull the blanking solution 344 into the interface chip 102 may be user defined. Once the flow of the blanking solution 344 into the interface chip 102 is complete, the system controller 348 may control the blanking robot of the preparation stage to move to the blanking well and pick up the next blanking slug. However, as illustrated in FIG. 7, in some alternative embodiments, the flow controller 350 may draw the blanking solution 344 into the interface chip 102 in a step (e.g., step S707) separate from the step S704 in which PCR amplification is performed.

Figure 8I:
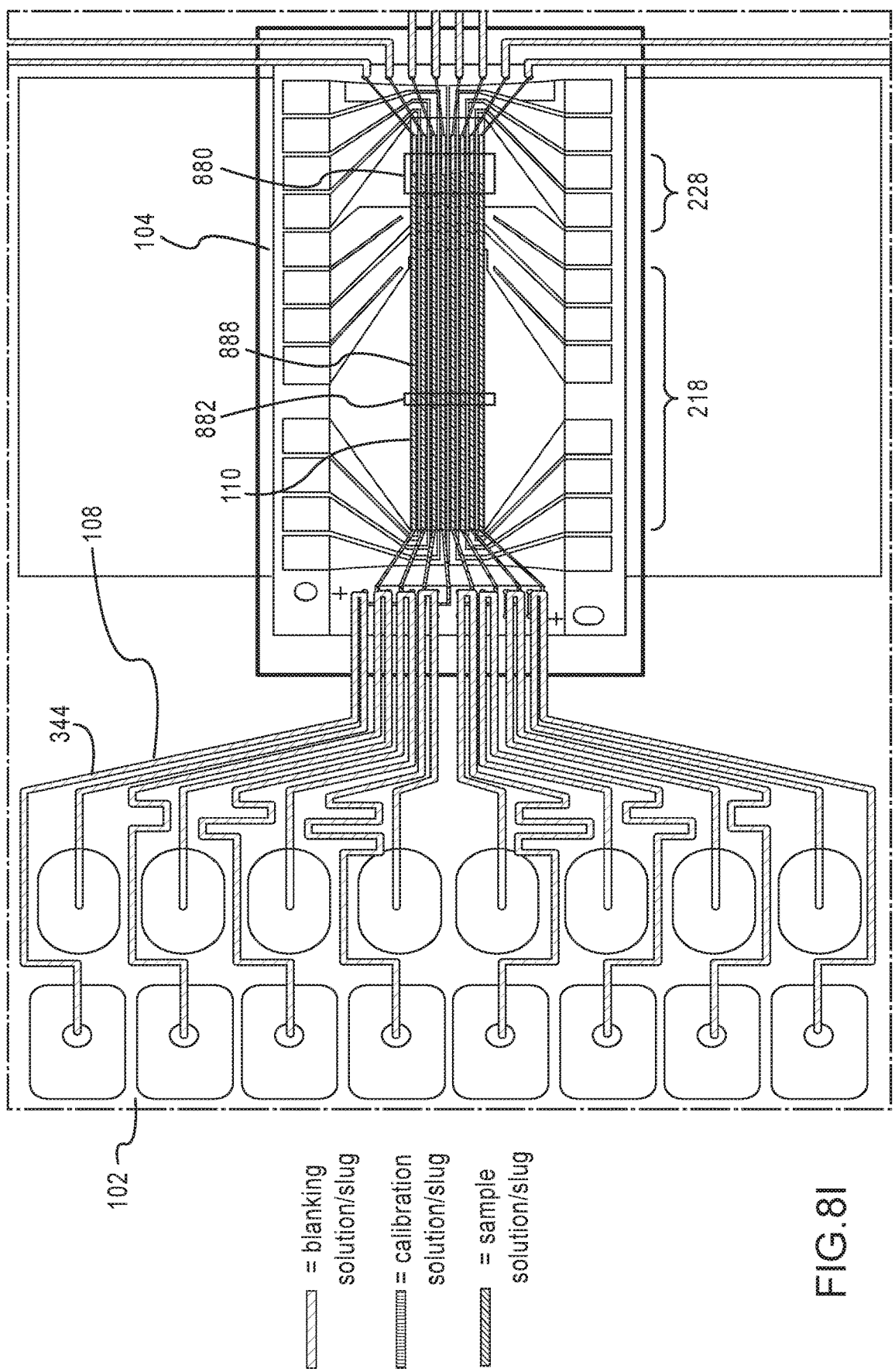

FIG. 8I illustrates an example of the blanking solution 344 drawn into the one or more channels 108 of the interface chip 102 during the step S704 or S707. A detailed example of the processing that may be performed in step S704 (including drawing blanking solution 344 into the interface chip 102) is illustrated in FIG. 9B with reference to the "K Blank Asp CL" and "PCR" steps.

In some embodiments, the single slug process 700 for performing the PCR amplification and melt data acquisition may include a step S705 in which the heating controller 352 controls the one or more heating elements 220 to heat a portion of the sample slug 888 in a thermal zone 218 of the reaction chip 104 according to a temperature ramp profile. In some embodiments, the detection system 354 may control the thermal zone detection device 376 to measure fluorescence from the portion of the sample slug in the thermal zone 218.

In step S705, the detection system 354 may briefly excite a camera of the thermal zone detection device 376 to capture a full frame snapshot which is used to perform a camera sync operation. In one embodiment, the detection system 354 may set the camera settings to melt mode and, during the melt, the camera may store high speed images in a melt data buffer. The detection system 354 may turn on thermal zone excitation device 374 (e.g., one or more blue LEDs) to its melt (high power) settings. The heating elements 220 associated with the thermal zone 218 are allowed to settle to the minimum temperature used in thermal ramp (see the "S" label in the "Melt" step of FIG. 9B). Then, the heating controller 352 may execute a temperature ramp in thermal zone 218 (Zone 1). In a non-limiting embodiment, the temperature range and ramp rate of the temperature ramp profile may be user defined and may be stored in a database of the system 300.

In some embodiments, in step S705, the single slug system 300 may perform an optional second melt (i.e., the double melt option). If the double melt option is selected in the system control, the system 300 will execute a second melt in step S705. In the second melt, the heating controller 352 may set the heating elements 220 to the minimum temperature used in the temperature ramp.

In a non-limiting embodiment of the second melt, the detection system 354 may turn off one or more blue LEDs of thermal zone excitation device 374, images may be read from the buffer, and fluorescence intensities may be calculated from the PCR/melt ROIs 1098 in the first thermal zone 218. In the second melt, temperature data may be combined with image data using a melt preprocessor, and a melt curve may be presented to the user.

Following the analysis of the first melt, the detection system 354 may excite a camera of the thermal zone detection device 376 to capture a full frame snapshot which is used to perform a camera sync operation (i.e., synchronize the clocks of the camera and system controller 348). In one embodiment, the detection system 354 may set the camera settings to melt mode and, during the melt, the camera may store high speed images in a melt data buffer. The detection system 354 may turn on one or more blue LEDs of the thermal zone excitation device 374 to its melt (high power) settings. The heating elements 220 associated with the thermal zone 218 may be allowed to settle to the minimum temperature used in thermal ramp (see the "S" label in the "Melt" step of FIG. 9B). Then, the heating controller 352 may execute a temperature ramp in thermal zone 218 (Zone 1). In a non-limiting embodiment, the temperature range and ramp rate of the temperature ramp profile may be user defined and may be stored in a database of the system 300.

During step S705 (i.e., during both melt and an optional second melt), the detection system 354 may track the trailing edge of the blanking slug 878 (e.g., via the U-flow ROIs 1016), and the flow controller 350 may control the position of the sample slug 888 based on feedback from the detection system 354 to hold the trailing edge of the blanking slug 878 at a target location with the slug building target region 880. In this way, the sample slug 888 may be held in the microfluidic channel 110 of the reaction device 104.

A detailed example of the processing that may be performed in step S705 (including the optional $2^{nd}$ melt processing) is illustrated in FIG. 9B with reference to the "Melt" and "Optional $2^{nd}$ melt" steps.

In some embodiments, the single slug process 700 for performing the PCR amplification and melt data acquisition may include a step S706 in which the system 300 repeats steps S701 through S705 if there are more samples 310 in the queue for analysis. If another sample 310 is to be analyzed and the flow controller 350 drew blanking solution 344 into the channels 108 of the interface device 102 in step S704, then process 700 may proceed to step S701. However, if another sample 310 is to be analyzed in an embodiment where the blanking solution 344 has not yet been drawn into the channels 108 of the interface device 102 in a step separate from a step in which PCR is performed, then the process 700 proceeds to a step S707, where the flow controller 350 draws blanking solution 344 into the channels 108 of the interface device 102.

In a non-limiting embodiment, in cycles 2-N of process 700 (i.e., when steps S701 through S705 are repeated for one or more additional samples), in step S701, the melt data analyzer 356 may analyze the melt data acquired the previous melt in step S705. In one embodiment, one or more melt curves may be presented in display of the system 300. However, in some embodiments, the process 700 does not require completion of the melt analysis before moving on the next step because the melt data has already been acquired. An example of processing including melt data analysis that may be performed in step S701 is illustrated in FIG. 9B with reference to the "U Blank Asp CL" step.

Figure 8J:
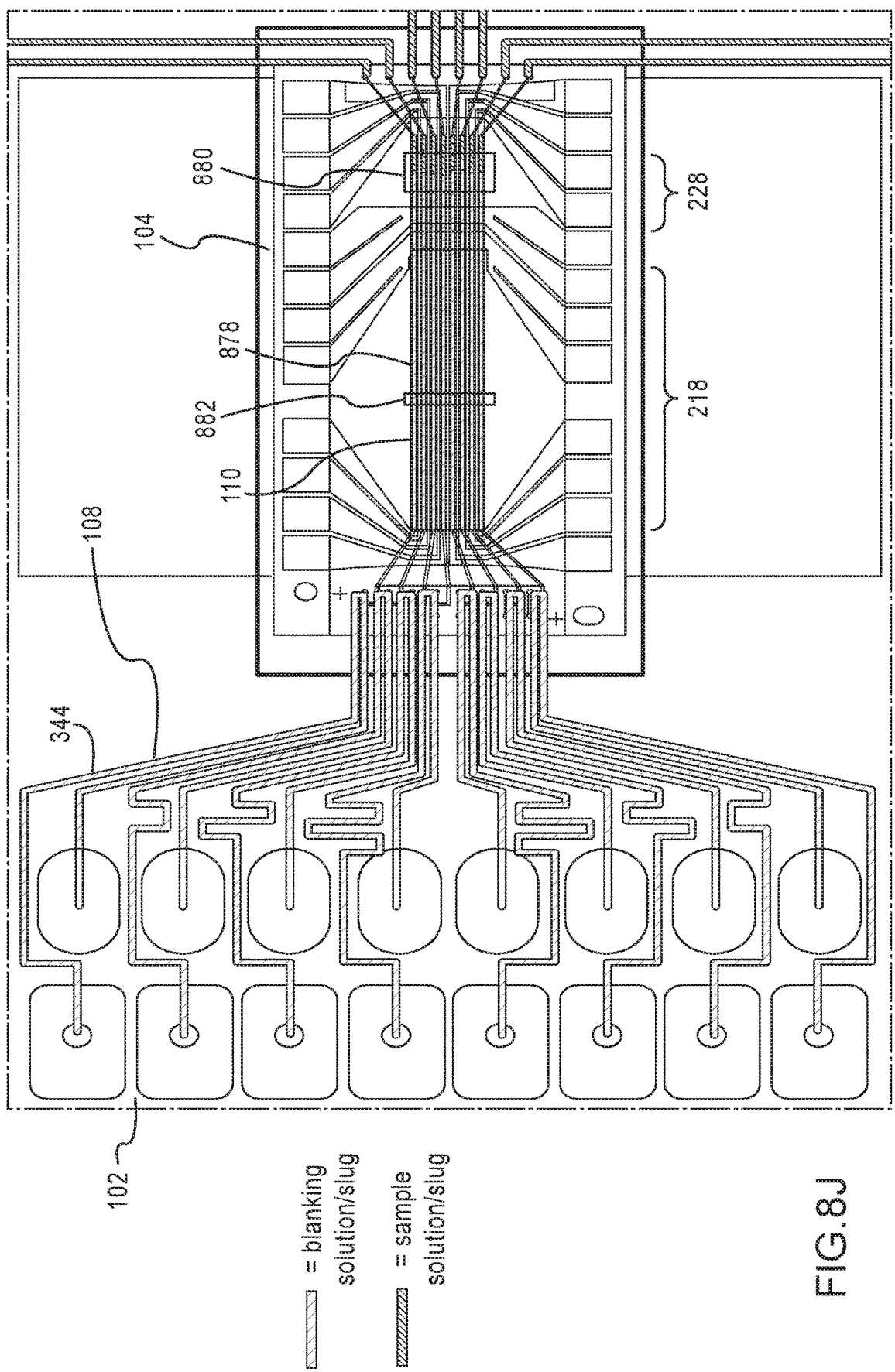
Figure 8K:
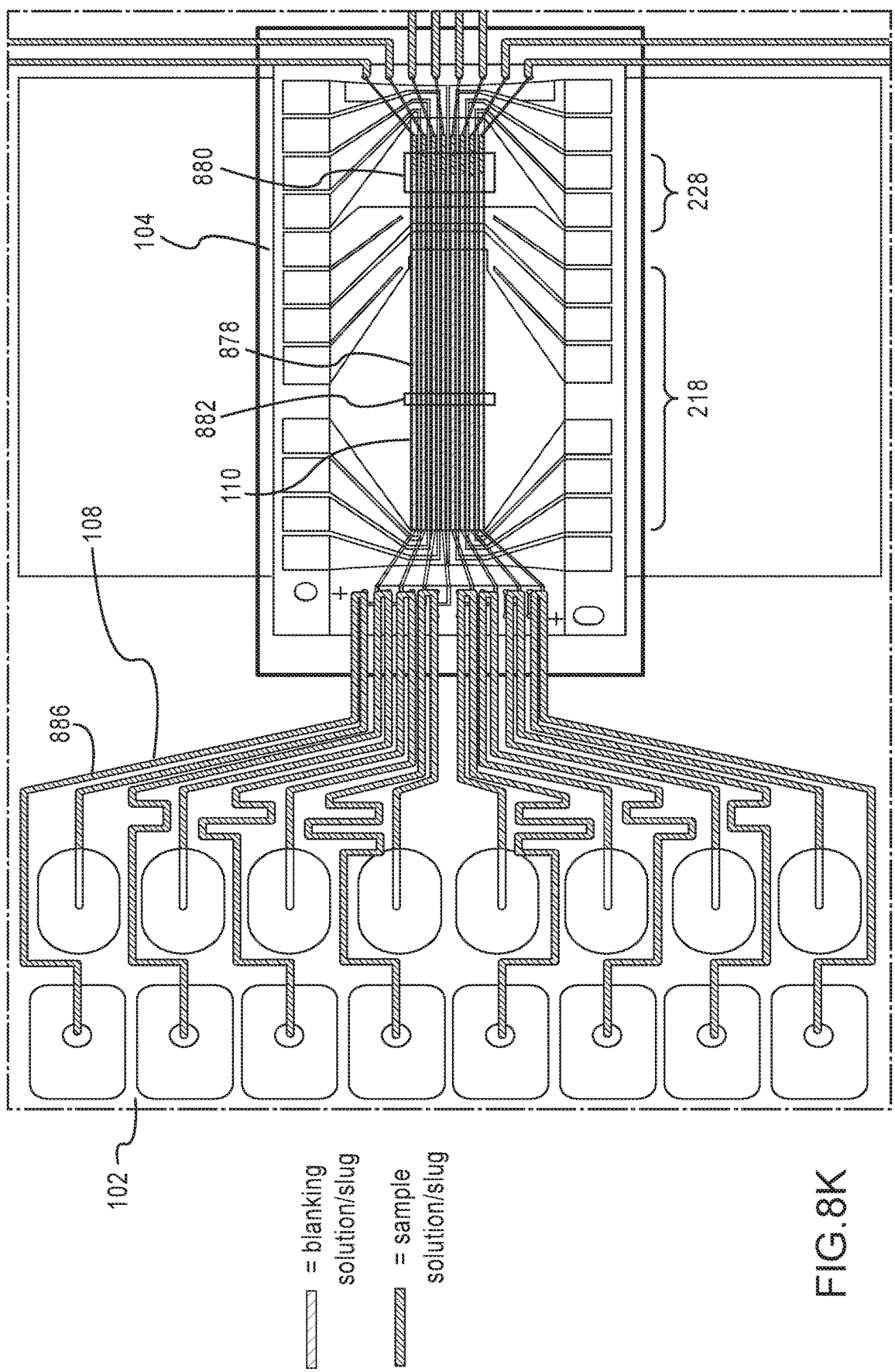
Figure 8L:
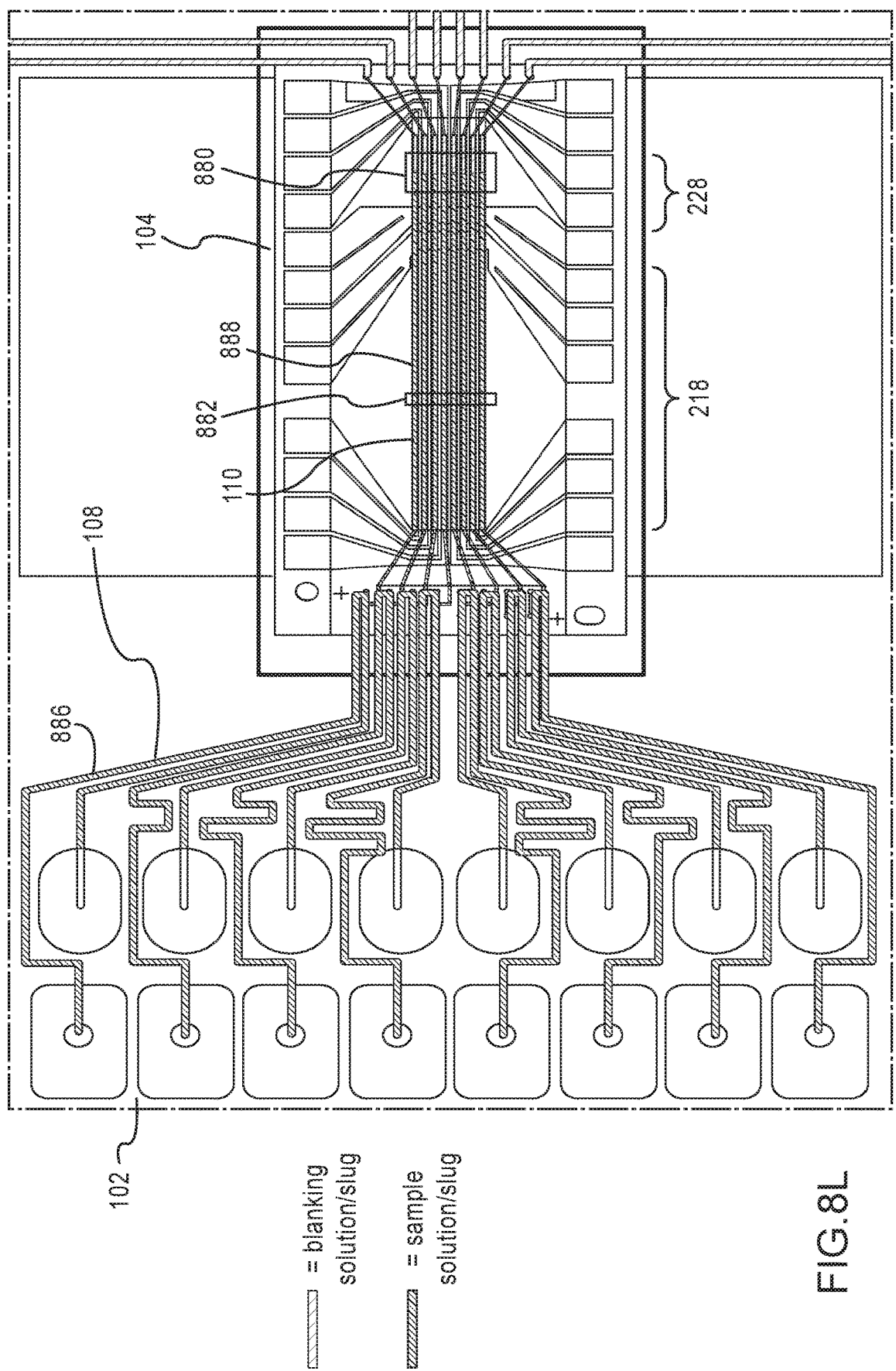

FIG. 8J illustrates an example of the blanking slug 878 built in the one or more channels 110 of the reaction chip 104 during a repeated step S701 with a leading edge in the slug building target region 880. FIG. 8K illustrates an example of the sample solution 886 drawn into the one or more channels 108 of the interface chip 102 during a repeated step S702. FIG. 8L illustrates an example of the sample slug 888 built in the one or more channels 110 of the reaction chip 104 during a repeated step S703.

Figure 11:
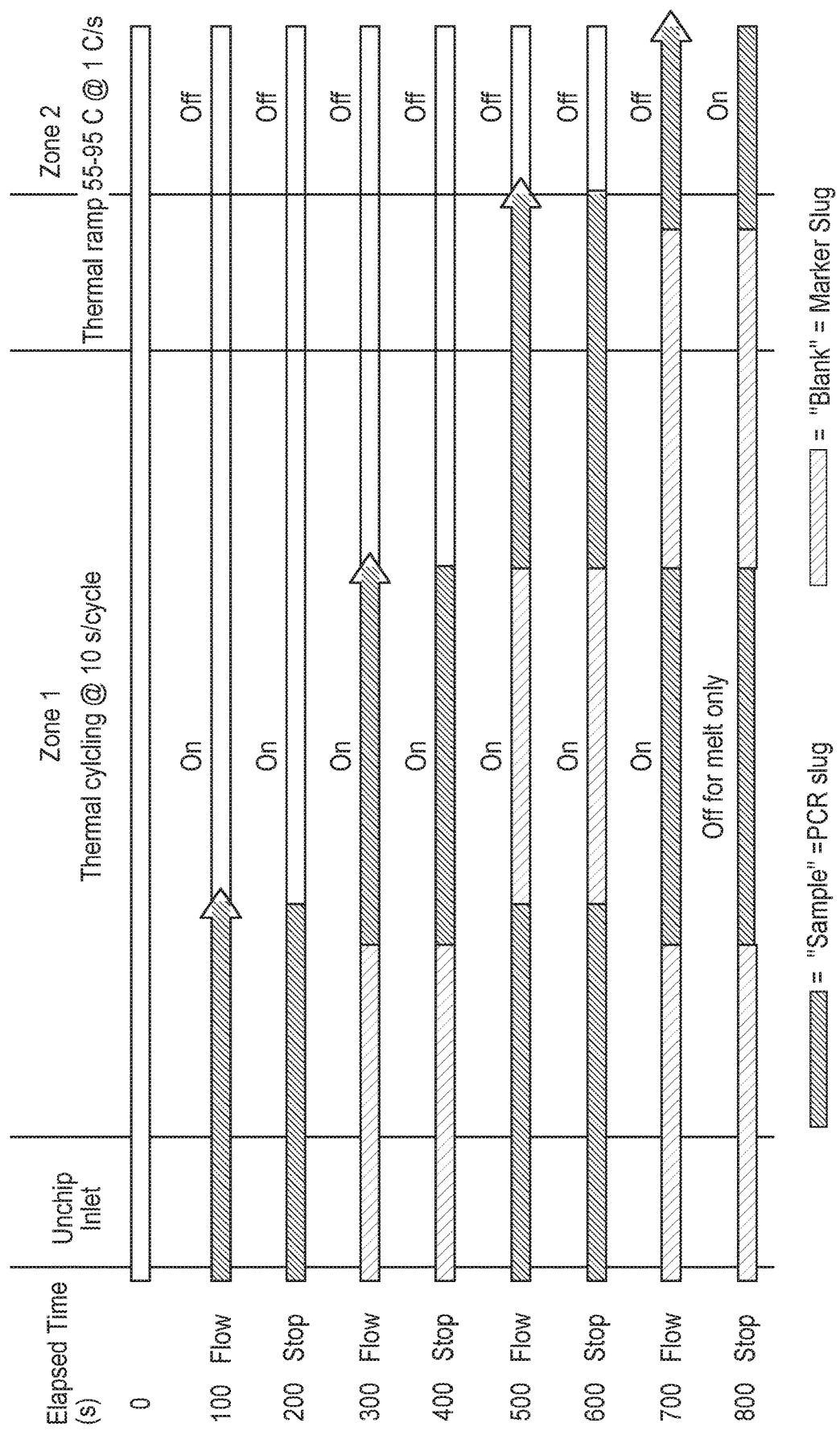
FIG. 11 illustrates a timing sequence of slugs progressing through a channel in a multi-slug system in accordance with the prior art.

For comparison with the exemplary slugs of the single slug system shown in FIGS. 8A-8L and the single slug timing shown in FIG. 9B, multiple short slugs created in each reaction chip channel of a multi-slug system is illustrated in FIGS. 10A-10E of U.S. Patent Application Publication No. 2012/0058519, which is incorporated by reference herein in its entirety, and FIG. 11 of U.S. Patent Application Publication No. 2012/0058519 illustrates a multi-slug timing diagram.

In some embodiments, aspects of the single slug approach performed by the system 300 may provide improvements relative to the multi-slug system in terms of flexibility, reliability, test throughput, and/or data quality, as described herein.

For example, a multi-slug system cannot use a "hot start" PCR amplification because multiple sample slugs could be in the thermal zone at the same time. However, the single slug system 300 may perform hot starting because only one sample slug (per channel) is in the thermal zone 218 of the reaction chip at a time.

The single slug system 300 may run distinct PCR cycles (e.g., a different PCR cycle for each sample slug 888 that passes through a channel 110 of the reaction chip 104) because the slug may be stopped in the center of the thermal zone 218 (Zone 1) (or the portion of the slug to be analyzed remains substantially in Zone 1, as in intermittent or creeping motion). In contrast, the multi-slug system cycles the slug as it enters and leaves Zone 1 so there is not a precise cycle count. With the single slug system 300, any number of cycles can be used (e.g., 35, 40, 35, 50, 60, etc.).

The single slug system 300 system may be run with slower ramp rates for melt analysis if desired. The multi-slug system is capable of running slower ramp rates like the single slug system 300, but there is a time constraint because flow and PCR happen concurrently. With single slug system 300, rates of 0.05° C./s, 0.3° C./s, 0.5° C./s, 1° C./s, and others have been used successfully.

While the multi-slug system can use different cycling profiles, the single slug system 300 may make it easier to change the profile because PCR may be decoupled from flow and melt. Tests utilizing the single slug approach may be run with 2 s, 8 s, 10 s, 15 s, 20 s, and other profiles.

The uncoupling of steps in the single slug approach may result in enhanced flexibility and a much simpler system. For example, with the single slug approach any number of PCR cycles may be used, and the PCR cycle times may be adjusted on an assay by assay basis. Similarly, the melting time may be lengthened to increase data quality or shortened to improve throughput. Also, real time PCR is possible in embodiments of the single slug system.

In some embodiments, the single slug system may be designed to enable recursive testing (reflex). That is, in some embodiments, the single slug system may provide the ability to change the conditions of a subsequent test or assay, based on the outcome of a previous test or assay, in a rapid, easy, and/or automated fashion. Such a feature would be useful for the application of mutation scanning followed by genotyping, such as, for example, as is described in U.S. patent application Ser. No. 13/172,104, which is incorporated by reference herein in its entirety.

Several aspects of embodiments of the present invention utilizing the single slug approach may specifically address data quality, such as, for example: (1) using a single large sample slug 888 that spans the thermal zone 218 (see, e.g., FIGS. 8H, 8I, and 8L); (2) calibration in slugs (e.g., stopped flow calibration); (3) the possibility of performing PCR in a stopped position; (4) melting the product in the thermal zone 218 (Zone 1) without any unnecessary fluid movement following PCR; (5) the potential to add a short "hot start" of the PCR master mix (to separate double-stranded human genomic DNA and activate the hot start enzyme) before the PCR thermal cycling; (6) the ability to use PCR cycles of any duration (including, e.g., much longer PCR cycles); (7) the ability to use any number of PCR cycles (e.g., a full 60 cycles to ensure more complete PCR); (8) the ability to provide an option for a denature/renature step immediately before melt analysis; (9) the ability to use any ramp rate for melt analysis (e.g., 0.1° C./s); and/or (10) the ability to perform a first melt followed by a second melt as a countermeasure to low frequency melt artifacts (e.g., dropped frames or other unexplained events).

In addition, the large size of the sample slug may eliminate the need for precise slug alignment and makes the slug training process obsolete.

Under the single slug approach, the long length of the sample slug 888 (relative to the short slugs of the multi-slug approach) may act as a buffer since the analysis will only focus on the PCR product at the center of thermal zone 218 (Zone 1). Furthermore, the focusing on the center of the thermal zone 218 in some of embodiments of the invention may be a simple countermeasure for several known issues. First, the focusing on the center of the thermal zone 218 may address uniformity of temperature across the length of thermal zone 218 because the temperature must only be uniform across the PCR/melt region of interest 1098, which may be, for example, 0.625 mm, rather than the entirety of thermal zone 218 (e.g., 14.75 mm). Second, red/green color cross talk, where the red signals suppress the green signal, is inherent under the multi-slug approach, but, in embodiments of the single slug system, this interference may be reduced because the PCR/melt region of interest (ROI) 1098 far from the red blanking slug 878. Third, embodiments of the single slug system may address slug edge effects because (i) diffusion/dispersion of the reagents and PCR product may be mitigated by extending the length between the PCR/melt ROIs 1098 and the boundary of the sample slug 888 in the slug building target region 880, (ii) analyzing the PCR product in the center of the thermal zone 218 (Zone 1) without moving it to a different thermal zone for melt data analysis may eliminate the possibility of losing product through dispersion (which would occur if the product were moved to the second zone 228 (Zone 2), and (iii) motion artifacts in melt curves due to unwanted slug movements may be eliminated by having similar fluid (i.e., extra sample solution) on either side of the PCR/melt ROI 1098.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A method for performing polymerase chain reaction (PCR) amplification and melt data acquisition in a single slug reaction system, the method comprising:
    building a blanking slug by drawing a blanking solution into a microfluidic channel of a reaction chip of a microfluidic device until the leading edge of the blanking slug reaches a blanking slug building target region;
    building a sample slug by drawing a sample solution into the microfluidic channel of the reaction chip of the microfluidic device until the trailing edge of the blanking slug reaches a sample slug building target region;
    heating a portion of the sample slug in a thermal zone of the reaction chip to cycle the temperature of the portion of the sample slug in the thermal zone according to a PCR amplification profile;
    heating the portion of the sample slug in the thermal zone of the reaction chip according to a temperature ramp profile; and
    during heating of the portion of the sample slug in the thermal zone according to the temperature ramp profile, measuring fluorescence from the portion of the sample slug in the thermal zone.

2. The method of claim 1, further comprising performing a melt analysis to identify the melting temperature of a nucleic acid in the sample slug based on the fluorescence from the portion of the sample slug in the thermal zone measured during heating of the portion of the sample slug in the thermal zone according to the temperature ramp profile.

3. The method of claim 1, wherein the blanking slug is a first blanking slug, the sample slug is a first sample slug, the sample solution is a first sample solution, and the method further comprises:
    building a second blanking slug by drawing the blanking solution into the microfluidic channel of the reaction chip of the microfluidic device until the leading edge of the second blanking slug reaches the blanking slug building target region;
    building a second sample slug by drawing a second sample solution into the microfluidic channel of the reaction chip of the microfluidic device until the trailing edge of the second blanking slug reaches the sample slug building target region;
    heating a portion of the second sample slug in the thermal zone of the reaction chip to cycle the temperature of the portion of the sample slug in the thermal zone according to the PCR amplification profile;
    heating the portion of the sample slug in the thermal zone of the reaction chip according to the temperature ramp profile; and
    during heating of the portion of the second sample slug in the thermal zone according to the temperature ramp profile, measuring fluorescence from the portion of the second sample slug in the thermal zone.

4. The method of claim 3, further comprising:
    performing a first melt analysis to identify the melting temperature of a nucleic acid in the first sample slug based on the fluorescence from the portion of the first sample slug in the thermal zone measured during heating of the portion of the first sample slug in the thermal zone according to the temperature ramp profile; and
    performing a second melt analysis to identify the melting temperature of a nucleic acid in the second sample slug based on the fluorescence from the portion of the second sample slug in the thermal zone measured during heating of the portion of the second sample slug in the thermal zone according to the temperature ramp profile.

5. The method of claim 1, further comprising calibrating the microfluidic device.

6. The method of claim 5, wherein calibrating the microfluidic device comprises:
    building a calibration blanking slug by drawing a calibration blanking solution into the microfluidic channel of the reaction chip of the microfluidic device until the leading edge of the calibration blanking slug reaches the blanking slug building target region;
    building a calibration test slug by drawing a calibration solution including a known sample into the microfluidic channel of the reaction chip of the microfluidic device until the trailing edge of the calibration blanking slug reaches the sample slug building target region;
    heating the portion of the calibration test slug in the thermal zone of the reaction chip according to the temperature ramp profile;
    during heating of the portion of the calibration test slug in the thermal zone according to the temperature ramp profile, measuring fluorescence from the portion of the calibration test slug in the thermal zone; and
    performing a calibration melt analysis to determine calibration coefficients.

7. The method of claim 6, wherein the calibration melt analysis is a first calibration melt analysis, and calibrating the microfluidic device additionally comprises:
    heating the portion of the calibration test slug in the thermal zone of the reaction chip according to the temperature ramp profile a second time;
    during heating of the portion of the calibration test slug in the thermal zone according to the temperature ramp profile for the second time, measuring fluorescence from the portion of the calibration test slug in the thermal zone;

performing a second calibration melt analysis to verify whether the calibration coefficients were correctly determined.

8. The method of claim 1, further comprising:
heating, for a second time, the portion of the sample slug in the thermal zone of the reaction chip according to the temperature ramp profile;
during the second heating of the portion of the sample slug in the thermal zone according to the temperature ramp profile, measuring fluorescence from the portion of the sample slug in the thermal zone; and
performing a melt analysis to identify the melting temperature of the nucleic acid in the sample slug based on the fluorescence from the portion of the sample slug in the thermal zone measured during the first heating of the portion of the sample slug in the thermal zone and the fluorescence from the portion of the sample slug in the thermal zone measured during the second heating of the portion of the sample slug in the thermal zone.

9. The method of claim 1, wherein the reaction chip comprises a second zone, and slugs in the microfluidic channel of the reaction chip reach the second zone after passing through the thermal zone.

10. The method of claim 9, wherein one or both of the blanking slug building target region and the sample slug building target region is within the second zone of the reaction chip.

11. The method of claim 10, wherein the second zone is a second thermal zone.

12. The method of claim 9, wherein the second zone is a second thermal zone.

13. The method of claim 12, wherein the microfluidic chip comprises a first heating element associated with the thermal zone and a second heating element associated with the second zone, the first heating element is used to heat the portion of the sample slug in the thermal zone of the reaction chip according to the PCR amplification and temperature ramp profiles.

14. The method of claim 9, wherein the microfluidic chip comprises a heating element associated with the thermal zone, the first heating element is used to heat the portion of the sample slug in the thermal zone of the reaction chip according to the PCR amplification and temperature ramp profiles, and the microfluidic chip does not comprise a heating element associated with second zone.

15. The method of claim 1, wherein the sample slug is held in a fixed position during heating of the portion of the sample slug in the thermal zone according to the PCR amplification and temperature ramp profiles.

16. The method of claim 1, further comprising, after building the sample slug, holding the sample slug in position until after heating of the portion of the sample slug in the thermal zone according to the temperature ramp profile is completed.

17. The method of claim 1, further comprising, after building the sample slug and before completion of heating of the portion of the sample slug in the thermal zone according to the temperature ramp profile, drawing the sample slug across the thermal zone, wherein the sample slug is drawn across the thermal zone with a flow rate slow enough that the sample slug remains in the thermal zone for the entirety of the heating according to the PCR amplification and temperature ramp profiles.

18. The method of claim 1, further comprising, after building the sample slug and before completion of heating of the portion of the sample slug in the thermal zone according to the temperature ramp profile, intermittently moving the sample slug.

19. The method of claim 1, further comprising, after building the sample slug and before completion of heating of the portion of the sample slug in the thermal zone according to the temperature ramp profile, moving the sample slug back and forth in the microfluidic channel of the reaction chip of the microfluidic device.

20. The method of claim 1, wherein the measured fluorescence from the portion of the sample slug in the thermal zone is measured only from a region of interest within the thermal zone.

21. The method of claim 20, wherein the region of interest is small relative to the size of the thermal zone.

22. The method of claim 20, wherein the region of interest is in the center of the thermal zone.

23. The method of claim 20, wherein the region of interest is within the middle 50% of the thermal zone.

24. The method of claim 20, wherein the region of interest is located at the portion of the thermal zone where PCR amplification is most efficiently carried out.

25. The method of claim 1, further comprising, during heating of the portion of the sample slug in the thermal zone of the reaction chip according to the PCR amplification profile, measuring fluorescence from the thermal zone.

26. The method of claim 25, further comprising, during heating of the portion of the sample slug in the thermal zone of the reaction chip according to the PCR amplification profile, adjusting the PCR amplification profile based on the measured fluorescence.

27. The method of claim 26, wherein adjusting the PCR amplification profile comprises adjusting the number of temperature cycles of the PCR amplification profile or adjusting denaturation, annealing, or extension temperatures of the PCR amplification profile.

28. The method of claim 25, wherein the measured fluorescence from the portion of the sample slug in the thermal zone during heating according to the PCR amplification profile is measured only from a region of interest within the thermal zone.

29. The method of claim 28, wherein the measured fluorescence from the portion of the sample slug in the thermal zone during heating according to the temperature ramp profile is measured only from the region of interest within the thermal zone.

30. The method of claim 28, wherein the region of interest is small relative to the size of the thermal zone.

31. The method of claim 28, wherein the region of interest is in the center of the thermal zone.

32. The method of claim 28, wherein the region of interest is within the middle 50% of the thermal zone.

33. The method of claim 28, wherein the region of interest is located at the portion of the thermal zone where PCR amplification is most efficiently carried out.

34. The method of claim 1, wherein the PCR amplification profile is a hot start PCR amplification profile.

35. The method of claim 1, wherein, during heating according to the PCR amplification and temperature ramp profiles, the sample slug completely fills the thermal zone of the reaction chip.

36. The method of claim 1, wherein the heating according to the PCR amplification and temperature ramp profiles is carried out using a heating element.

37. The method of claim 36, wherein the heating element is a thin film resistive heater associated with the microfluidic channel in the reaction chip of the microfluidic device.

38. The method of claim 37, wherein the thin film resistive heater associated with the microfluidic channel is adjacent to the microfluidic channel.

39. The method of claim 1, further comprising, after building the blanking slug and before building the sample slug, holding the leading edge of the blanking slug in position at the blanking slug building target region.

40. The method of claim 39, wherein the leading edge of the blanking slug is held in place using image based feedback control.

41. The method according to claim 1, further comprising, after building the sample slug and before completion of heating according to the temperature ramp profile, holding the trailing edge of the blanking slug in position at the sample slug building target region.

42. The method of claim 41, wherein the trailing edge of the blanking solution is held in place using image based feedback control.

43. The method of claim 1, wherein the blanking slug building target region and sample slug building target region are the same region.

44. The method of claim 1, wherein heating the portion of the sample slug in the thermal zone of the reaction chip according to the PCR amplification profile cycles the temperature of the portion of the sample slug in the thermal zone of the reaction chip through denaturation, annealing, and extension temperatures.

45. The method of claim 1, further comprising:
drawing the blanking solution into a microfluidic channel of an interface chip of the microfluidic device via an inlet port of the interface chip, wherein the blanking solution drawn into the microfluidic channel of the reaction chip of the microfluidic device to build the blanking slug is drawn from the microfluidic channel of the interface chip;
drawing the sample solution into the microfluidic channel of the interface chip of the microfluidic device via the inlet port of the interface chip, wherein the sample solution drawn into the microfluidic channel of the reaction chip of the microfluidic device to build the sample slug is drawn from the microfluidic channel of the interface chip.

46. The method of claim 45, wherein drawing the blanking solution into the microfluidic channel of the reaction chip of the microfluidic device comprises filling a T-junction with the blanking solution from the microfluidic channel of the interface chip and drawing the blanking solution into the microfluidic channel of the reaction chip from the T-junction;
wherein drawing the sample solution into the microfluidic channel of the reaction chip of the microfluidic device comprises filling the T-junction with the sample solution from the microfluidic channel of the interface chip and drawing the sample solution into the microfluidic channel of the reaction chip from the T-junction.

47. The method of claim 46, wherein the reaction chip comprises the T-junction.

48. The method of claim 46, further comprising determining whether the blanking solution has filled the T-junction by detecting whether a leading edge of the blanking solution has reached a region of interest in the interface chip of the microfluidic device.

49. The method of claim 46, further comprising determining whether the sample solution has filled the T-junction by detecting whether a trailing edge of the blanking solution has reached the region of interest in the interface chip of the microfluidic device.

50. The method of claim 1, wherein the blanking slug building target region and sample slug building target region are within a region of interest in the reaction chip of the microfluidic device.

51. The method of claim 1, further comprising, after heating the portion of the sample slug in a thermal zone of the reaction chip to cycle the temperature of the portion of the sample slug in the thermal zone according to the PCR amplification profile and before heating the portion of the sample slug in the thermal zone of the reaction chip according to the temperature ramp profile, heating the portion of the sample slug in the thermal zone of the reaction chip according to a de-naturing and re-naturing profile.

52. A microfluidic device comprising:
at least one microfluidic channel configured to receive a carrier fluid and a sample slug, the sample slug containing polymerase chain reaction (PCR) reagents;
a thermal element in thermal communication with a first zone of the at least one microfluidic channel;
a controller configured to control the thermal element to thermocycle the sample slug in the microfluidic channel to perform a PCR reaction followed by a high resolution thermal melt (HRTM) in the first zone of the microfluidic channel; and
a detector configured to detect a fluorescent signal from the sample slug located in the microfluidic channel,
wherein the controller is configured to independently adjust operating parameters of the PCR reaction for consecutive slugs.

53. The microfluidic device of claim 52, wherein a length of the sample slug limits the at least one microfluidic channel to having a single sample slug.

54. The microfluidic device of claim 52, wherein adjusting operating parameters associated with the PCR reaction for each sample slug includes optimizing a PCR amplification profile and a ramp temperature profile of the melt analysis based upon the fluorescent signal.

55. The microfluidic device of claim 52, wherein the controller is configured to stop the sample slug in the microfluidic channel for performing the PCR reaction and the melt analysis.

56. The microfluidic device of claim 52, wherein the controller is configured to perform the PCR reaction and the melt analysis on a flowing sample slug.

57. The microfluidic device of claim 52, wherein the microfluidic channel includes the first zone and a second zone, the first zone is in thermal communication with the thermal element, and the second zone is outside the first zone.

58. The microfluidic device of claim 57, wherein the controller is configured to control a position of the sample slug by controlling a position of a leading edge of the sample slug located in the second zone of the microfluidic channel.

59. The microfluidic device of claim 52, wherein the length of the sample slug fills the microfluidic channel with a single sample slug and a single carrier fluid slug.

60. A method for processing a sample slug in a microfluidic device comprising:
loading a sample slug containing polymerase chain reaction (PCR) reagents and followed by a carrier fluid slug into at least one microfluidic channel;
thermocycling the sample slug in the microfluidic channel to perform a PCR reaction, wherein the PCR reaction is performed in a first zone of the microfluidic channel;

following thermocycling, performing a melt analysis, wherein the melt analysis is performed in the first zone of the microfluidic channel;

detecting a fluorescent signal from the sample slug in the microfluidic channel; and independently adjusting operating parameters of the PCR reaction for consecutive sample slugs.

61. The method of claim 58, wherein a length of the sample slug limits the at least one microfluidic channel to having a single sample slug.

62. A system comprising:

at least one microfluidic channel to perform a polymerase chain reaction (PCR) followed by a melt analysis on a sample slug containing PCR reagents, wherein the PCR reaction and the melt analysis are performed in a first zone of the at least one microfluidic channel; and an image sensor having a first image sensor region having a first field of view and a second image sensor region having a second field of view, wherein the second field of view is different than the first field of view, at least a portion of the first zone is within the first field of view to detect a signal associated with the PCR reaction and the melt analysis, and a leading edge of the sample slug bordering with a carrier fluid slug is within the second field of view during the PCR reaction and the melt analysis.

63. The system of claim 62, wherein the first field of view detects the signal from a center of the first zone.

64. A microfluidic device comprising:

at least one microfluidic channel to receive a sample slug containing polymerase chain reaction (PCR) reagents;

a heating system in thermal communication with a first region of the microfluidic channel to thermocycle the sample slug in the first region of the microfluidic channel to perform a PCR reaction and to ramp the temperature of the sample slug in the first region of the microfluidic channel to perform a melt analysis;

wherein the first region of each microfluidic channel is limited to having a single sample slug at any point in time during the PCR reaction and the melt analysis, wherein a thermocycling profile and operating parameters of the PCR reaction are individually adjusted for each sample slug based upon a fluorescent signal resulting from the thermocycling.

* * * * *